(12) United States Patent
Perez

(10) Patent No.: US 11,918,769 B2
(45) Date of Patent: *Mar. 5, 2024

(54) APPLICATOR AND SYSTEM FOR ADMINISTERING AND DISPENSING FLOWABLE PHARMACEUTICAL PREPARATIONS

(71) Applicant: TICKERWORKS, INC., Folsom, CA (US)

(72) Inventor: Ramiro M. Perez, Folsom, CA (US)

(73) Assignee: TICKERWORKS, INC., Folsom, CA (US)

(*) Notice: Subject to any disclaimer, the term of this patent is extended or adjusted under 35 U.S.C. 154(b) by 777 days.

This patent is subject to a terminal disclaimer.

(21) Appl. No.: 16/729,187

(22) Filed: Dec. 27, 2019

(65) Prior Publication Data

US 2020/0129743 A1 Apr. 30, 2020

Related U.S. Application Data

(63) Continuation of application No. 16/004,701, filed on Jun. 11, 2018, now abandoned, which is a continuation of application No. 14/997,553, filed on Jan. 17, 2016, now Pat. No. 10,471,242, which is a continuation-in-part of application No. 14/042,588, filed on Sep. 30, 2013, now abandoned, which is a continuation-in-part of application No. 13/275,282, filed on Oct. 17, 2011, now Pat. No. 8,544,684.

(60) Provisional application No. 61/443,029, filed on Feb. 15, 2011.

(51) Int. Cl.
| | | |
|---|---|---|
| A61M 31/00 | (2006.01) | |
| A61K 31/565 | (2006.01) | |
| A61K 31/57 | (2006.01) | |
| G01F 13/00 | (2006.01) | |
| A61M 35/00 | (2006.01) | |

(52) U.S. Cl.
CPC ........... *A61M 31/00* (2013.01); *A61K 31/565* (2013.01); *A61K 31/57* (2013.01); *G01F 13/00* (2013.01); *A61M 35/003* (2013.01); *A61M 2205/19* (2013.01); *A61M 2205/582* (2013.01); *A61M 2205/583* (2013.01)

(58) Field of Classification Search
CPC ........... B67D 99/00; B67D 5/42; A61M 31/00
See application file for complete search history.

(56) References Cited

U.S. PATENT DOCUMENTS

| | | |
|---|---|---|
| 2,907,496 A | 10/1959 | Carstensen |
| 3,333,740 A | 8/1967 | Waller |
| 3,549,057 A | 12/1970 | Perez |
| 3,616,970 A | 11/1971 | Baumann et al. |
| 3,862,748 A | 1/1975 | Grise |
| 3,873,008 A | 3/1975 | Jahn |
| 4,074,833 A | 2/1978 | Otto, Sr. |
| 4,139,127 A | 2/1979 | Gentile |
| 4,298,036 A | 11/1981 | Horvath |
| 4,363,560 A | 12/1982 | Gentile |
| 4,521,127 A | 6/1985 | Tomburo et al. |
| 4,544,083 A | 10/1985 | Schroeder |
| 4,595,124 A | 6/1986 | Duval et al. |
| 4,641,776 A | 2/1987 | Vlasek et al. |
| 4,658,993 A | 4/1987 | Vlasich |
| 4,850,516 A | 7/1989 | Seager |
| 4,865,231 A | 9/1989 | Wiercinski |
| 5,000,356 A | 3/1991 | Johnson et al. |
| 5,007,755 A | 4/1991 | Thompson |
| 5,016,782 A | 5/1991 | Pfanstiel |
| 5,025,960 A | 6/1991 | Seager |
| 5,397,178 A | 3/1995 | Konietzko |
| 5,540,361 A | 7/1996 | Fattori |
| 5,573,341 A | 11/1996 | Iaia |
| 5,725,133 A | 3/1998 | Iaia |
| 5,839,622 A | 11/1998 | Bicknell et al. |
| 5,851,079 A | 12/1998 | Horstman et al. |
| 5,947,621 A | 9/1999 | Szekely |
| 6,039,483 A | 3/2000 | Szekely |

(Continued)

FOREIGN PATENT DOCUMENTS

| | | |
|---|---|---|
| WO | WO 93/23156 | 11/1993 |
| WO | WO 02/26369 | 4/2002 |
| WO | WO 02/087986 | 11/2002 |

OTHER PUBLICATIONS

Holtorf, K et al. Holtorf Medical Group, "The Bioidentical Hormone Debate: Are Bioidentical Hormones (Estradiol, Estill, and Progesterone) Safer or More Efficacious than Commonly Used Synthetic Versions in Hormone Replacement Therapy?" Torrance, CA: US (2009).

Johnson, Michael L. and Veldhuis, Johannes D., "Quantitative Neuroendocrinology: Methods in Neuroscience." San Diego, CA: US (1995).

(Continued)

*Primary Examiner* — Micah Paul Young

(74) *Attorney, Agent, or Firm* — Knobbe Martens Olson & Bear LLP

(57) ABSTRACT

A transdermal delivery apparatus for delivering specific desired quantities of cream-base medicament or any flowable composition is disclosed. The apparatus comprises a revolving platform, a threaded screw-complex, a house, an applicator pad, and a safety cap. The revolving platform produces audible and tactile sensations upon interaction with projections from the house. The threaded screw-complex interacts with an elevator to transport the medicament upwards. The house confines an inner chamber to store the medicament. The applicator pad comprises a center outlet where the composition exits the chamber.

14 Claims, 20 Drawing Sheets

(56) References Cited

U.S. PATENT DOCUMENTS

| | | |
|---|---|---|
| 6,375,047 B1 | 4/2002 | Herda |
| 6,450,720 B1 | 9/2002 | Cai |
| 7,086,564 B1 | 8/2006 | Corrigan |
| 7,213,994 B2 | 5/2007 | Phipps et al. |
| 7,303,348 B2 * | 12/2007 | Phipps ................ A61M 35/003 222/391 |
| 7,399,113 B2 | 7/2008 | Konietzko |
| 7,751,934 B2 | 7/2010 | Konietzko |
| 7,879,830 B2 | 2/2011 | Wiley |
| 7,946,780 B2 | 5/2011 | Zhang |
| 8,292,532 B2 | 10/2012 | Nasu et al. |
| 8,544,684 B2 * | 10/2013 | Perez ...................... G01F 13/00 401/175 |
| 2004/0118879 A1 | 6/2004 | Konietzko |
| 2004/0180866 A1 | 9/2004 | Mamchur |
| 2005/0224137 A1 | 10/2005 | Tribble et al. |
| 2008/0223479 A1 | 9/2008 | Bassett et al. |
| 2010/0217176 A1 | 8/2010 | Carrara et al. |
| 2012/0205000 A1 | 8/2012 | Phipps |
| 2012/0269029 A1 | 10/2012 | Konietzko |
| 2016/0129228 A1 | 5/2016 | Perez |

OTHER PUBLICATIONS

Lokkegaard, E et al. Institute of Public Health, University of Copenhagen, "Hormone therapy and risk of myocardial infarction: a national register study." Copenhagen, DK (2008).

Scharfman, H et Maclusky, N, "Estrogen-Growth Factor Interactions and Their Contributions to Neurological Disorders." Orangeburg, NY: US (2009).

Carey et al., A study to evaluate serum and urinary hormone levels following short and long term administration of two regimens of progesterone cream in postmenopausal women British Journal of Obstetrics and Gynaecology, Jun. 2000, vol. 107, pp. 722-726.

Hammarback, Stefan et al., "Cyclical mood changes as in the Premenstrual tension Syndrome during Sequential Estrogen Progestagen Postmenopausal Replacement Therapy." Acta Obstetricia et Gynecologica Scandinavica 64.5 (1985): 393-397, abstract only.

* cited by examiner

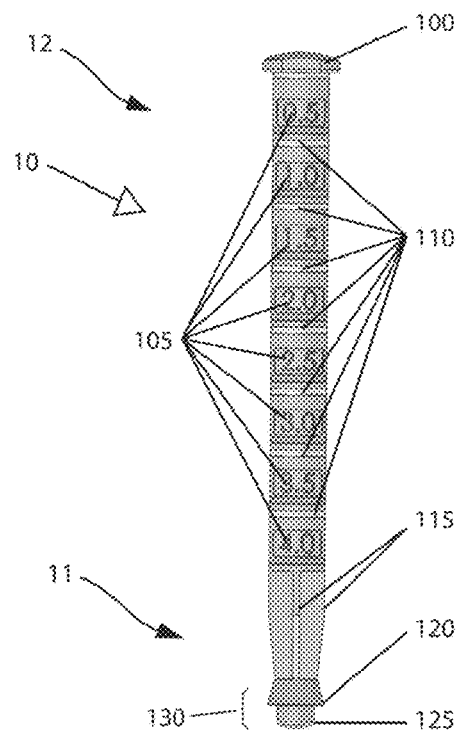

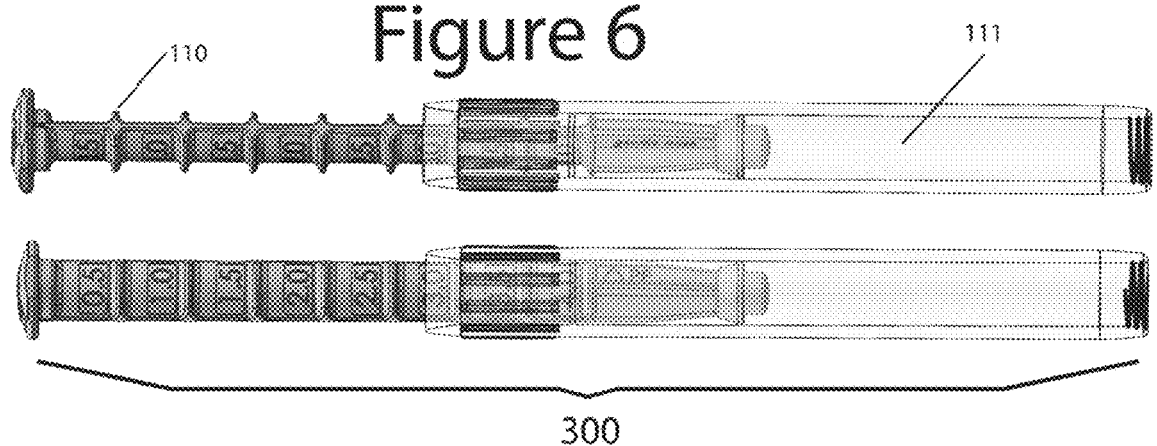
Figure 6
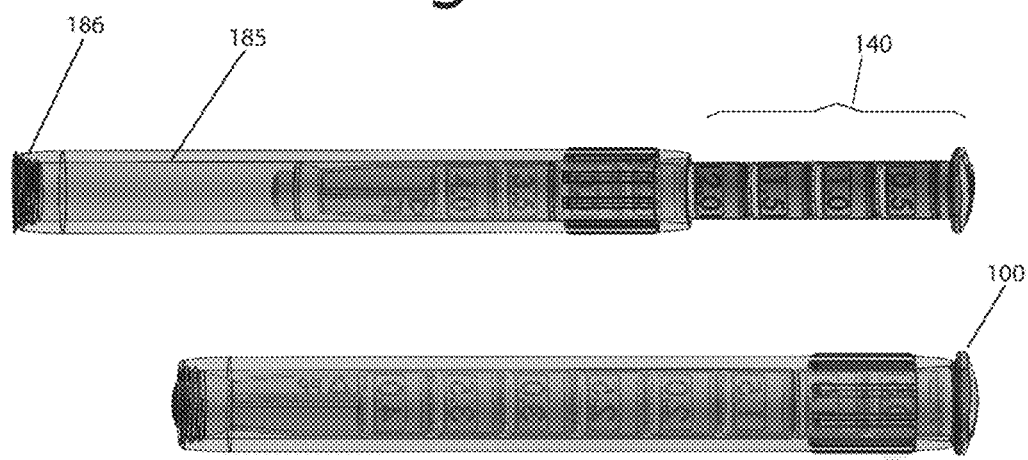
Figure 7A
Figure 7B
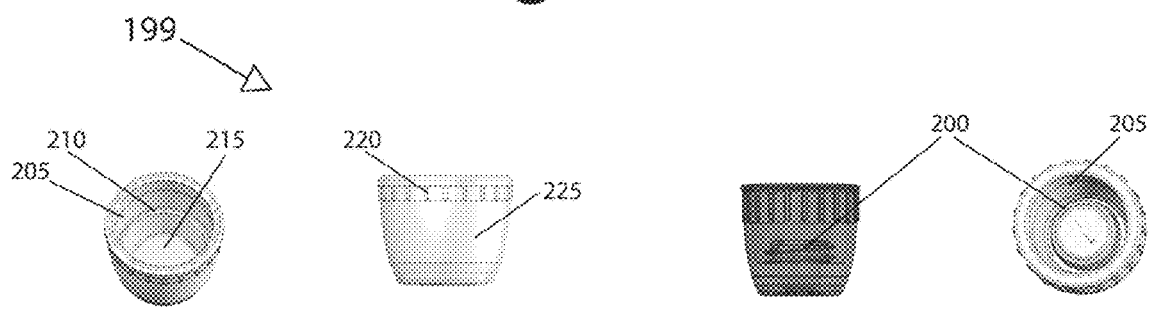
Figure 8
Figure 9

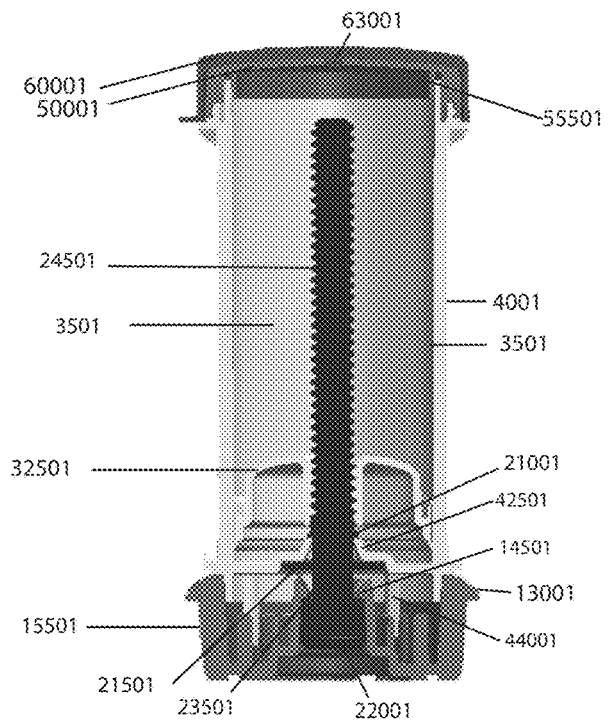
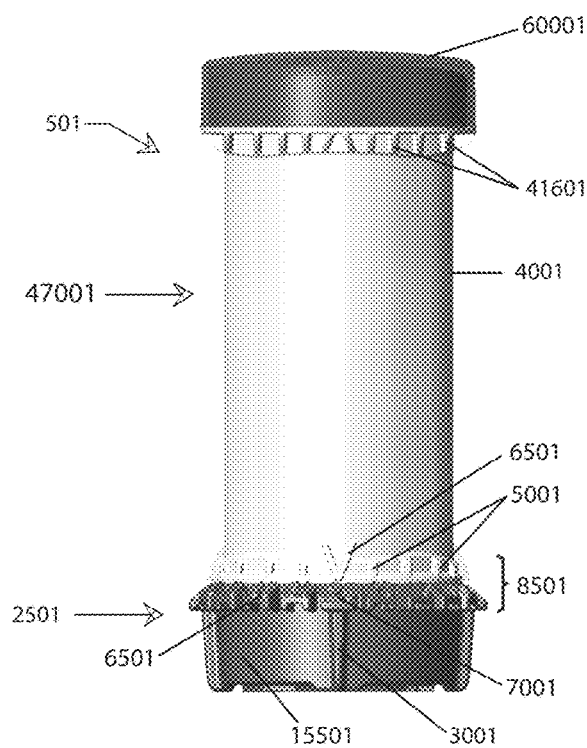
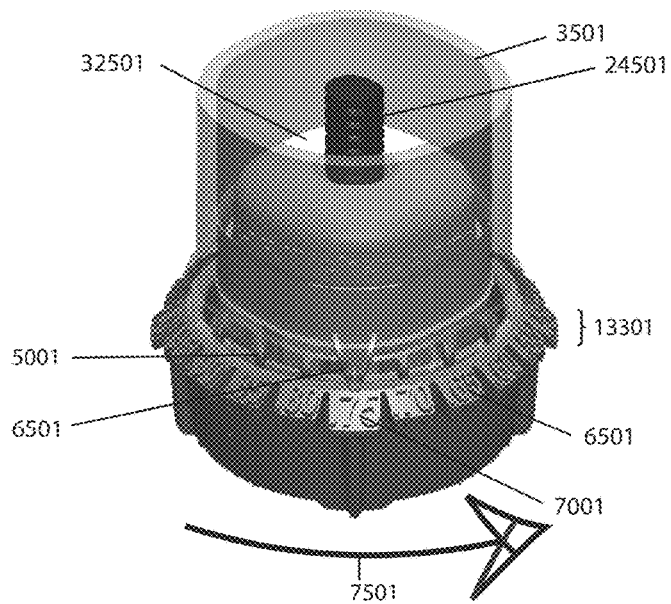

Rear View

Front View

Top View

APPLICATOR AND SYSTEM FOR ADMINISTERING AND DISPENSING FLOWABLE PHARMACEUTICAL PREPARATIONS

CROSS-REFERENCE TO RELATED APPLICATIONS

The present application is a continuation of U.S. patent application Ser. No. 16/004,701, filed on Jun. 11, 2018, which is a continuation of U.S. patent application Ser. No. 14/997,553, filed on Jan. 17, 2016, which is a non-provisional continuation-in-part patent application claiming priority to U.S. patent application Ser. No. 14/042,588, filed on Sep. 30, 2013, which is a non-provisional continuation-in-part patent application claiming priority to U.S. patent application Ser. No. 13/275,282, filed on Oct. 17, 2011, now U.S. Pat. No. 8,544,684, which is a non-provisional U.S. patent application claiming priority to provisional patent application Ser. No. 61/443,029, filed on Feb. 15, 2011. The present continuation patent application claims priority to the referenced patent applications, each of which is hereby incorporated by reference herein in their entirety.

TECHNICAL FIELD

The various embodiments described herein relate to an applicator for inserting flowable pharmaceutical preparations into a body cavity, an adapter for connecting a jar to a cavity dispenser, a jar dispenser with a nozzle for automated transferring and dispensing of flowable pharmaceutical compositions, and a metered dial-dispenser configured to connect to a cavity dispenser for humans and animals.

A dispenser is disclosed for flowable cream-base medicaments, specifically, a unidirectional rotatable platform attached to a screw that is slipped into a barrel where it is secured in place and it joins the said components that house an elevator. Upon clockwise rotation of the rotatable platform against the barrel, the elevator rises, and a fixed amount of flowable composition discharges from an output orifice in the center of the dispenser.

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2009-2019 Ramiro M. Perez, All Rights Reserved.

BACKGROUND

One of the greatest challenges patients face today, is the ability to self-administer accurate and precise oral, topical, rectal, and vaginal dosages of prescribed flowable medications. The main culprit being the limitations posed by commercially available delivery systems. Furthermore, measuring the correct dosage of flowable drugs to be applied through these routes of administration in the older patient population, requires their ability to see the small, dye printed, faint numbers on the plunger of the applicator as it is with the prior arts. Similarly, self-application of an accurate and precise flowable dosage by the visually impaired patient population is also not presently possible. In addition, feedback mechanisms that ensure proper dosing in a metered, and tactile fashion are also non-existent. The ability to preload flowable custom drug dosages into a cavity applicator from piston driven jar dispensers, and also to protect from evaporation and contamination are also not presently available.

Standard vaginal applicators today generally consist of two parts: Barrel and plunger. Some companies distribute the vaginal applicator without applicator caps, while others do include them. Variations in vaginal applicators may comprise three components. Barrel, cap, and a plunger with a fused piston at the first end. The applicators generally are molded then delivered to a printing company where the plunger is imprinted with dosing ruler so that the patient would be able to read the information and apply the proper amount. Further handling of the parts beyond its manufactured institution is generally a problem for manufacturers as it increases costs, as well as the likelihood of damage and contamination of the parts.

Vaginal hormone preparations are generally packaged in plastic and aluminum tubes and used by older female patients generally during their perimenopausal, menopausal, and postmenopausal years of life. The patient is instructed to connect the tube to the vaginal applicator by screwing-on the applicator to the tube. Next, the patient applies pressure to the tube in order to fill the chamber of the vaginal applicator and causes the plunger of the applicator to rise. Once the desired dose is measured, the patient unscrews the applicator from the tube and inserts the measured dosage vaginally.

Expert physicians with advanced training in the functional and anti-aging community have repeatedly expressed that the present vaginal dispensers are too long to be properly inserted into the desired areas of the vaginal canal of women seeking hormone replacement therapy. In fact, in several cases the excess in length has caused trauma to the cervix and fornix. Lastly, the common applicator's shape is presently sub-optimal, painful, and it often lacks adequate anti-slippery holding regions, and depth indicators.

A delivery system that would offer visual, tactile, and metered dispensation is highly desirable to either transfer the flowable composition directly into the desired body area, or to a secondary applicator designed for the body cavities. Furthermore, a cavity dispenser that would offer clearly visible and tactile dosing segments with dosing tabs to facilitate feedback mechanisms is highly desirable, especially in the visually impaired population. These individuals would benefit from a reassuring dosing system that would allow them to feel the dosing segments on the plunger for measuring the proper dosage with their hands and fingers prior to applying the dosage.

American compounding pharmacists are increasingly dispensing hormone replacement therapy (HRT) cream-base medicines due to raised awareness of its safety profile and benefit in relieving symptoms of hormone imbalance. The challenge to dispense accurate amounts of cream-base medicine continues since delivery device options have been very limited. Not so long ago, a prevalent option for administering cream-based HRT employed the use of ⅛, or ¼ teaspoonfuls, (looking much like an ice-cream sampling spoons) partaking in a common practice called, "eye balling." Syringes are still commonly used today in the delivery of hormone replacement therapy; whereby the pressing of the plunger pushes the cream out of the chamber through the small syringe orifice (needle excluded), and the user is able to get the correct dose by counting number differences or the number of line markings passed by the indicator.

New metered only transdermal applicators have shown some interest amongst providers and consumers. For example, pumps have been extensively employed where the user depresses a pump that delivers a "somewhat" fixed volumetric amount. (There seems to be a' lot of skepticism on the actual accuracy of these devices, especially dosing differences from the first to the second pump). Furthermore, pharmacists and physicians often have to adjust their dosing by taking into account large and inadequate volumetric amounts delivered by these metered-only devices (i.e. 0.6, 0.7, 0.9 ml per pump). Needless to say, there is extensive variability between pumps.

U.S. Pat. No. 7,213,994 B2, as disclosed, allows for the delivery of a, "Predetermined" amount of cream through an opening in the cap. Basically, when the base is rotated 90° clockwise, an audible and tactile, "Click" is supposed to be heard translating to the delivery of a predetermined amount of cream. Furthermore, the patent claims a positive sensory feedback mechanism that confirms a desired amount of cream dispensed. The device is described as producing; in most cases, an audible sound upon a 90-degree clockwise rotation. However, consumers have reported a lack of audible sound or tactile feel on several cases, especially when the rotatable base is left in between clicking segments for prolonged periods of time; which makes it enormously difficult for consumers to apply a desired dose. The problem may be highly attributed to poor design, manufacturing defects, and poor quality assurance. To make matters worse, the said patent only delivers 0.476 g of cream-base medicament of a specific density per 180° displacement of the base past the barrel, (or per 2-clicks as reported by the company using the Medisca® HRT Cream Base). Thus, falling short from the needed 0.5 gram standard dosing requirement.

Although both types of metered only transdermal applicators have gained some popularity amongst U.S. compounding pharmacies, (especially if compared to other delivery devices, like syringes, metered screw-on caps, pea-sized spoons, etc.) the greatest challenge faced by these devices, is convincing users, and especially health providers that a "Click" or a "Pump" translates to a specific dose. Therefore, prescribers still refrain from writing in their scripts a dose based on clicks or pumps. Instead, for several decades, providers and patients seem to favor dosages based on a number scale or with some form of graduated line markings. Further, poor mechanical design, and 90 degrees, "click" limitations may be undesirable features to other consumers and providers. In this patent we have solved most the frustration medical prescribers and patients face today when it comes to selecting a useful device for delivering customary doses of transdermal hormone replacement therapies, as well as other uses unknown as of now. The present device offers consumers the delivery of calibrated volumetric amounts of cream-base medicament, a graduation area that allows consumers to visually measure a specified dose, the delivery of smaller, yet consistent volumes if desired, concurrent bi-audible, and bi-tactile features to provide dosing reassurance, and superior flexibility in the dosing of cream-base medicaments without the limitations of, "pumps" or, "clicks" posed by metered only devices

SUMMARY

The various embodiments described herein eliminate the necessity of imprinting on the plunger, as it has been done for decades. This novel applicator is constructed with largely visible dosing tabs and inter segments to the naked eye. Furthermore, in cases where the eyesight may be impaired, the dosing tabs and inter-segments are also easily identified by the sense of touch. Additionally, above each segment, an extruded number is also positioned in sequential numerical order to indicate the amount being applied. Another advantage the various embodiments described herein offer, is the ability to preload these applicators with multiple volumetric quantities such as 1, 2, 3, or 4 milliliters as necessary for the compounding laboratory.

A length-conscious cavity applicator for delivering flowable pharmaceutical preparations for hormone and other therapies built with visual, feedback, tactile, and metered mechanisms is disclosed. The ability to transfer flowable compositions from metered and non-metered piston-driven apparatuses into the smaller chambered cavity applicators through different types of connecting configurations or removable adapters are also disclosed herein. Lastly, a piston driven jar dispenser with a nozzle and cap configured for manual and automated dispensing is also disclosed herein.

With regard to the various embodiments described herein, a cavity applicator is provided for delivering accurate and precise dosages of flowable pharmaceutical preparations into the cavity of a human or animal. The cavity applicator comprises the hollow body to store the composition, plunger to push the contents inside the body cavity, and a cap to retard evaporation of the contents inside. The cavity applicator is loaded by larger piston-driven metered and non-metered containers directly or via adapter. The non-metered piston-driven jar dispensers consist of a barrel, a lid with a center outlet, and a push-piston to drive the contents to a secondary delivery system via a removable nozzle, or to a cavity applicator via a removable adapter. The metered container consists of a cap, barrel, dispensing lid with a central outlet, and a ratable base that is coupled to a screw that causes a piston to move upwards; thereby, also driving the contents into the desired chamber of the cavity applicator.

Several embodiments are disclosed, in which a novel device employs a unidirectional rotational mechanism where visual, audible, and tactile elements work together synergistically for the delivery of calibrated volumetric amounts of topical cream-base medicaments of a specified density, or any other flowable material if warranted. The interaction of primary and secondary ticker tabs stemming from the bottom exterior wall of the house, and corresponding major, minor, and redundant side ticks stemming from the rotatable platform; which, allows for the delivery of specific volumetric amounts of cream-base medicaments, has not been elucidated until now.

Moreover, the interaction and involvement of selective ticker tabs stemming from the clicking zone of the house and corresponding major, minor, and redundant side ticks stationed on the rotatable platform; which, are responsible for creating two different types of audible sounds and tactile sensations to the user depending on the angular displacement of the rotatable element against the house from a predetermined point of reference will be disclosed in detail.

The term 'housing element', or 'house' will be used to denote a barrel, side ticks as an alternative name to side tabs, and composition as an alternative name to cream-base medicament as disclosed. One example embodiment of the dispensing apparatus includes a unidirectional rotatable platform that engages the head-bolt of a left threaded screw-complex that can be slipped into the inner chamber of the housing element and secured in place by cooperation of a snap-ring and locking tabs located on the bottom wall of the house. Once inside, the screw interacts with an elevator that fits tightly against the wall of said inner chamber. Upon clockwise axial movement of the rotatable platform against the house, audible and tactile sensations can be perceived by the user at every 18 degrees of rotation. However, the type of sound depends if the 18° rotation of the platform is directed to a minor digit tab (minor tick note; soft click) or to a major digit tab (major tick note; louder sound) since different ticker tabs are involved and interact with major, minor, or redundant side ticks depending on the displacement of the rotatable platform against the house from a predetermined point of reference. The elevator rises and pushes upward the flowable contents of such chamber, exiting through an output orifice located at the center of a dispenser, which is secured to the upper end of the house providing a surface to apply the cream or gel directly onto the skin. A removable cap with a plug to retard evaporation of the cream-base medicament is stationed on top of the dispenser. As the platform rotates, the user is able to count the number of equispaced digit tabs on the rotatable platform past the markings on the first end of the house for determining a desired dose. A left threaded rod interacts with an elevator equipped with a top and bottom edge seal useful in preventing a cream smudge trail or any visible cream from being left behind and causes it to rise. A bi-audible mechanism is in place for determining set volumetric amounts dispensed upon an 18° clockwise rotation of the rotatable platform against the house. A 90°, 180°, 270°, or a 360 degree displacement of the rotatable platform against the house from a predetermined point of reference produces a peculiar audible and tactile sensation on the user, referred here as the first sound. Likewise, displacement other than a 90°, 180°, 270°, or 360 degrees from a predetermined point of reference, produces a different yet distinct audible and tactile sensation on the user, referred here as the second sound. An 18° rotation of the base platform translates to a 0.05 numerical difference on the exterior wall of the rotatable platform, or one digit tab movement of the rotator past the house. It follows that a 90° rotation translates to a 0.25 numerical difference on the exterior wall of the rotatable platform with respect to the house. The device has been configured to deliver roughly one gram of a specified cream of a specific density (or 1.03 g of water at 25° C.) for every 360° rotation of the rotatable platform against the house. A dispenser pad is available to aid in the application of the cream-base medicament if so desired by the consumer.

BRIEF DESCRIPTION OF THE DRAWINGS

The various embodiments are illustrated by way of example, and not by way of limitation, in the figures of the accompanying drawings in which:

FIG. 1 is a side view of the plunger; the top end is the distal end, and bottom end is the proximal end;

FIG. 2 is a side view of the barrel; the top end is the distal end, and bottom end is the proximal end;

FIG. 3 is a side view of the barrel with a threaded end on its proximal end;

FIG. 4 is a side view of the plunger with a 90 degree axial rotation with respect to the view shown in FIG. 1;

FIG. 5 is a cross sectional view of a barrel with calibrated rest segments;

FIG. 6 depicts a side view of a pair of semi-transparent barrels with the plungers inserted (Applicator caps excluded);

FIG. 7A is a side view of the barrel and plunger pushed to the 2.0 dosing interval (Applicator cap excluded);

FIG. 7B is a side view of the barrel with the plunger completely inserted into the barrel;

FIG. 8 depicts a top view and a side view of a non-threaded cavity applicator cap;

FIG. 9 depicts a side view and a top view of a threaded applicator cap;

FIG. 33A is a front perspective view of a complete assembled apparatus for dispensing any flowable composition in reference to the various embodiments;

FIG. 33B is a vertical cross sectional view of an assembled dispenser;

FIG. 33C is a magnified horizontal cross-sectional view of the bottom end of the assembled dispensing apparatus with an arrow positioned just below to indicate rotational orientation of the rotatable platform;

DETAILED DESCRIPTION

Figure 10A:
FIG. 10A is a side view of the complete cavity applicator assembly without calibrated rest segments or circular ramps.

In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, example embodiments relate to an applicator for inserting flowable pharmaceutical preparations into a body cavity, an adapter for connecting a jar to a cavity dispenser, a jar dispenser with a nozzle for automated transferring and dispensing of flowable pharmaceutical compositions, and a metered dial-dispenser configured to connect to a cavity dispenser for humans and animals. In the various embodiments described herein, example embodiments relate to length-conscious cavity applicator for delivering flowable pharmaceutical preparations for hormone and other therapies built with visual, feedback, tactile, and metered mechanisms. The ability to transfer flowable compositions from metered and non-metered piston-driven apparatuses into the smaller chambered cavity applicators through different types of connecting configurations or removable adapters are also disclosed herein. Lastly, a piston driven jar dispenser with a nozzle and cap configured for manual and automated dispensing is also disclosed herein. The details of these example embodiments are provided below.

Cavity Applicator and Cap

FIGS. 1 through 11 depict an example embodiment of the cavity applicator 300. We will solely make references to a cavity applicator from here on, but it is to encompass vaginal, rectal, oral, and other like sites of application in humans and animals. Furthermore, the applicator may also extend beyond the cavity sites of application to topical or transdermal delivery sites. In one embodiment, the plunger 10 that has been constructed as a robust dome seal complex 130 on its proximal end 11 connected through structural guiding ribs 115 to a segmented dosing area and a digit trigger 100 at the distal end 12. As the consumer exerts force on the digit trigger 100 of the plunger 10, it slides through the inner walls of the barrel 20. Meanwhile, at the proximal end 21 of the barrel 20, the piston seal 120 pushes the contents inside the chamber to exit through the outlet into the desired body cavity. The amount dispensed is equivalent to the number of dosing segments cleared against the distal end 22 of the barrel 20. As illustrated in FIG. 1, the plunger 10 is exposed in a side view where the dome-seal complex 130 comprises the piston seal 120 and the dome tip 125 at the proximal end 11 of plunger 10. The structural guiding ribs 115 make way to the dosing tabs 110 and to the inter-segments 135. Each inter-segment 135 houses an extruded number 105 to denote volume to be dispensed in milliliters. The preferred numbers are arranged sequentially, starting from the lowest at the top (0.5) and the highest at the bottom (4.0). Other fractional segments may be possible to configure. Likewise, the dosing interval 140 can be manufactured to be larger or smaller, and it will likely vary the size of the cavity applicator.

Figures 21A, 21B:
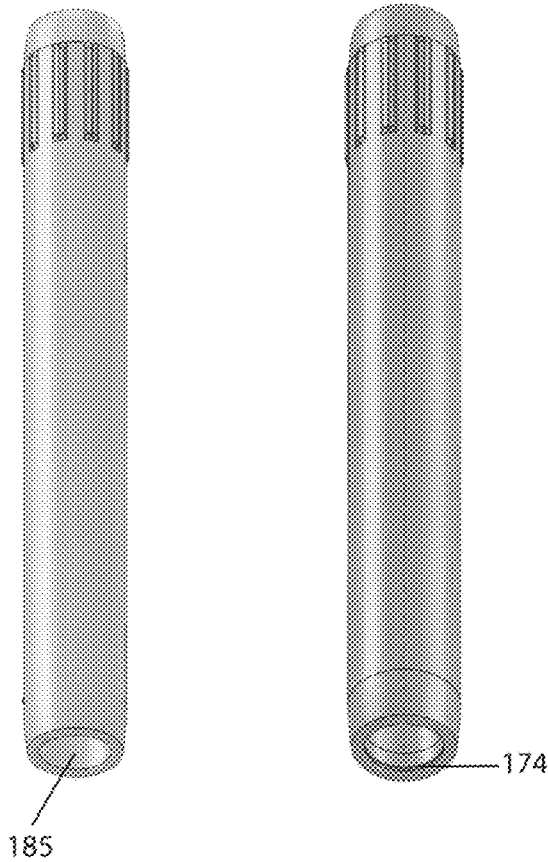
FIG. 21A is a bottom-side view of the barrel of the cavity applicator exposing the proximal end of the barrel, and the inner wall; note, there are no circular rims or threads in this configuration.
FIG. 21B is a bottom-side view of the barrel of the cavity applicator exposing the proximal end of the barrel, inner side wall, and a rim.

The barrel 20 of the cavity applicator 300 comprises an elongated, double-walled, hollow cylinder-like design. Other shapes may also be possible to manufacture if desired. The proximal end 11 of the plunger 10 gets inserted through the distal edge window 155 of the barrel 20, past the one way ramp 175 sliding through the inner wall 185 of the barrel 20. The barrel 20 has a thumb grip and depth indicator 160 at its distal end 22. Therefore, as it gets inserted to the depth where the thumb grip and depth indicator resides 160, the consumer will likely feel the ribs around the circumference of the applicator entering the cavity via sensory feedback mechanisms. The barrel body 165 can also be used to insert the applicator if desired for a shallower depth. In one of the embodiments as seen on FIG. 6 through 7B and FIG. 12 through 13, the proximal threaded end 170 of the barrel 20 screws to the distal screw 240 of the adapter 350. However, on a separate embodiment, FIG. 21A displays the proximal inner wall of the barrel 185 without threads or rims, and the mating takes place simply through a pressured slide in and slide out connecting mechanism. In contrast, FIG. 21B displays a rim indent 174 on the proximal end 21 of the barrel 20. Therefore, the proximal end 21 of the barrel 20 will slide into its mating counterpart, and then it will snap into place for a tighter connectivity.

In reference to FIG. 8, the proximal outer wall 186 of the barrel 20 slides through the inner side wall 205 of the cap 199 until it reaches the stopper 210 and it is bounded by the inner bottom wall of the cap 215. On a separate embodiment, FIG. 9 presents a screw-on version of the lid, where the inner bottom wall 215 of the cap houses a threaded screw 200 at its center, configured to screw with the proximal threaded end 170 of the barrel 20.

Figure 10B:
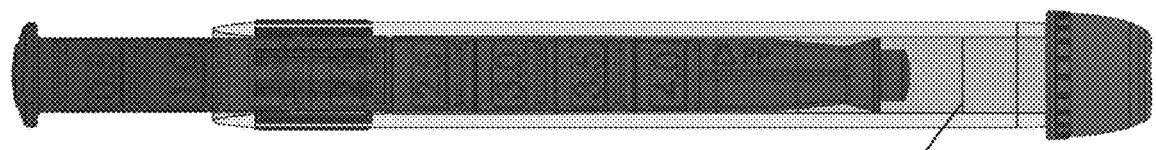
FIG. 10B is a side view of the complete applicator assembly with circular ramps.
Figure 11:
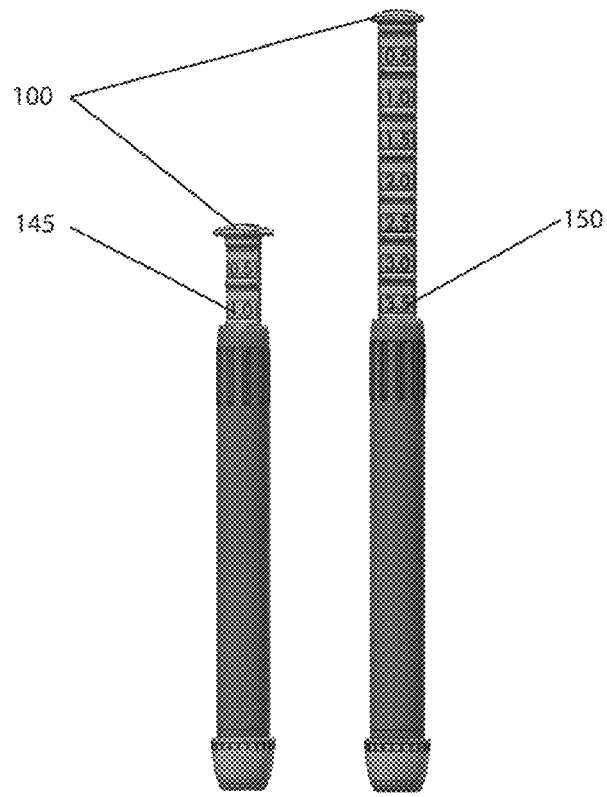
FIG. 11 depicts a side view of two complete applicator assemblies with different dosing intervals.

The barrel 20 may be configured to contain large and small volumetric quantities as generally desired, with a preferred maximum capacity between four to five milliliters and a preferred length between 100-110 millimeters. The plunger as illustrated in FIGS. 6 through 7B also has a preferred length between 100-110 millimeters. These metric values can be modified based on consumer and physician demands. Generally, a loading dosage ranging from two to four milliliters is first prescribed for the first weeks of therapy. Then, a smaller maintenance dosage is prescribed ranging from half to one milliliter. The example embodiments of FIGS. 6, 7A, 7B, 10A, 10B exhibit the applicator 300 configured with eight inter-segments 135 each bounded by its respective extruded visual and tactile dosing tab 110. Each dosing tab 110 is preferably configured to deliver a half-milliliter of pharmaceutical preparation and the cavity applicator shown is configured with a four milliliter total capacity. Alternatively, the applicator may be configured with larger or smaller dosing increments such as 0.25 ml or 0.125 ml based on consumer and physician demands. On a separate embodiment, FIG. 10A displays the barrel of the applicator without any circular segments 235. In contrast, on a separate embodiment, the inner wall 185 of the barrel 20 is equipped with a plurality of calibrated small circular extruded ramps 235 or circular hollow segments 195 as shown on FIG. 10B and FIG. 5 alongside the inner wall 185 of the barrel 20. Each of these ramps or segments represent a predetermined dosage which may be applied by the consumer. The ramps and rest segments facilitate feedback mechanisms and indicate a positional frame of reference of how much volumetric dosage has been applied. FIG. 10B displays eight calibrated circular rest segments 235 configured to interact with the piston seal 120 of the plunger 10 thus creating a feedback mechanism for the end user to indicate the dosage applied. The calibrated circular segments 195 and circular extruded ramps 235 of the barrel 20 of the cavity applicator 300 correspond with the linear displacement of the dosing tabs 110 on the plunger 10 against the distal edge window 155 of the barrel 20.

Figure 12:
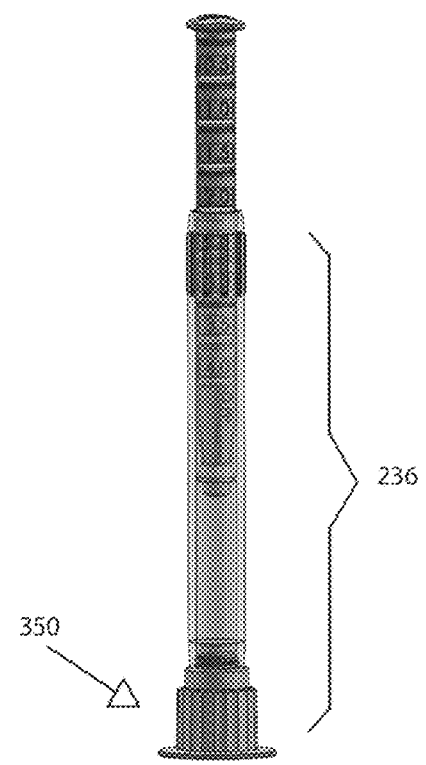
FIG. 12 depicts the plunger and barrel attached to an adapter.
Figure 13:
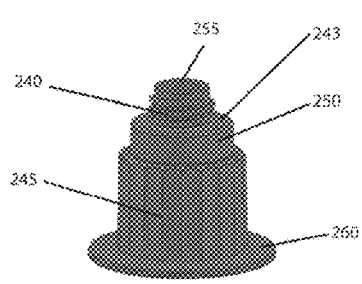
FIG. 13 is a side view of the adapter with a screw on its distal end.
Figure 14:
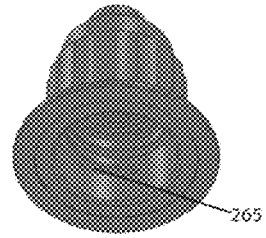
FIG. 14 depicts a bottom-side view of the adapter exposing the inner threads.
Figure 15:
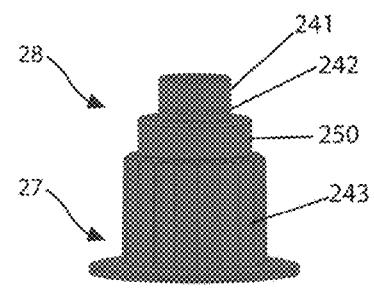
FIG. 15 depict a side view of the adapter with an adapter rim at the distal end.
Figure 16:
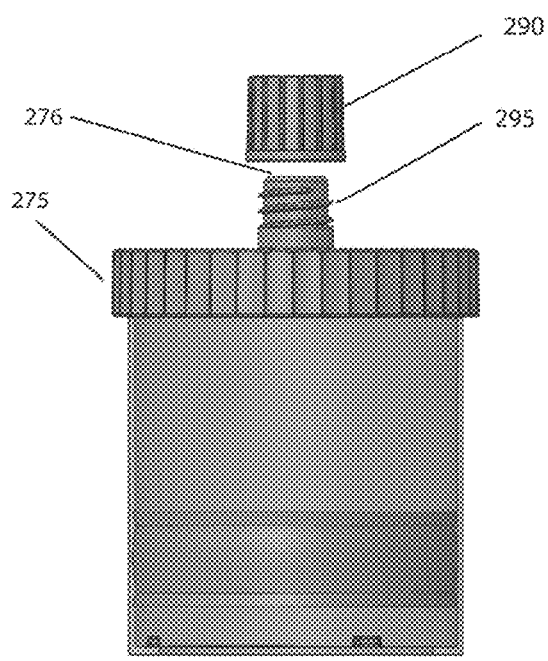
FIG. 16 is a side view of the jar with piston and a screwable lid attached; the screwable cap is also displayed right above the lid.
Figure 22A:
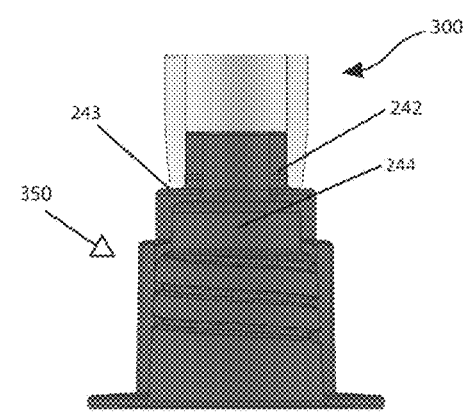
FIG. 22A depicts a cross section side view of the adapter attached to the cavity applicator and a rim at its distal end; the applicator slides into the adapter until it snaps into place for a tighter connection.
Figure 22B:
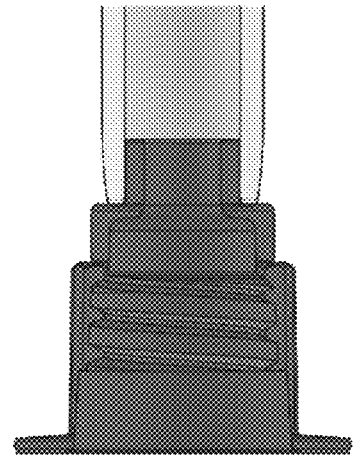
FIG. 22B depicts a cross-sectional side view of the adapter attached to the cavity applicator; the cavity applicator is configured to slide into and out of the adapter.
Figure 29:
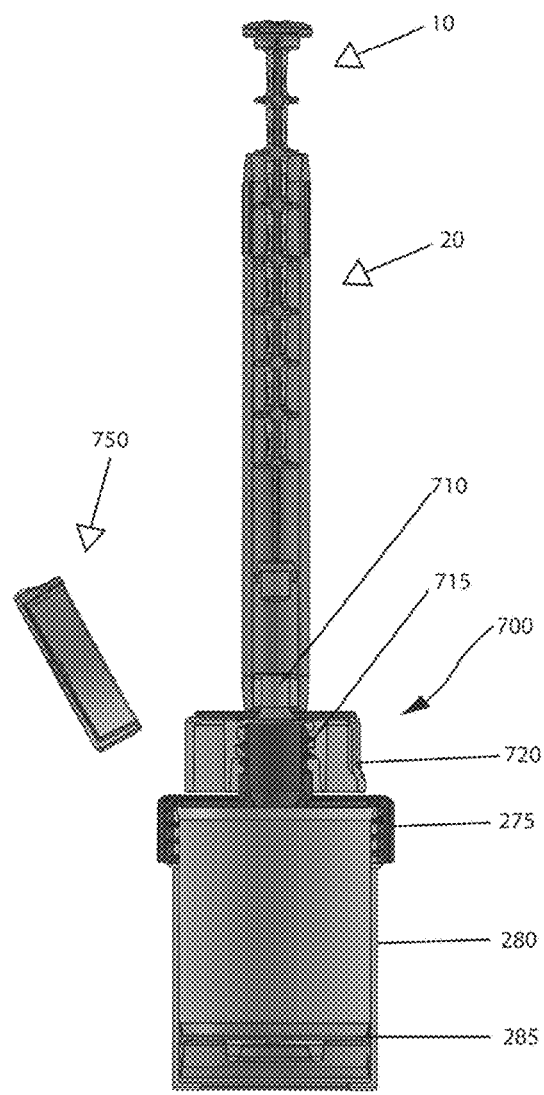
FIG. 29 is a side cross-sectional view of the dispenser jar, flip-cap adapter, and cavity applicator.
Figure 30:
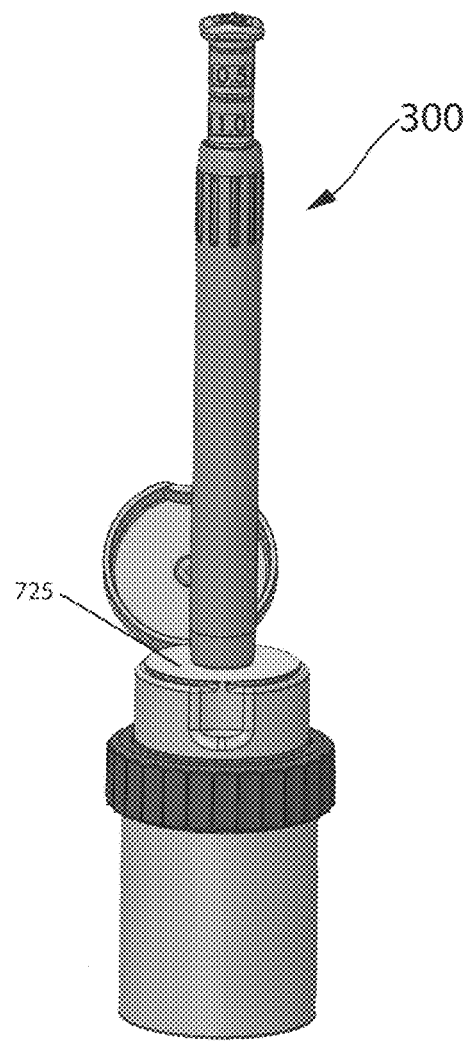
FIG. 30 is a side view of the dispenser jar, flip cap adapter, and cavity dispenser.

In another embodiment, FIG. 12 shows the mating mechanism between the cavity applicator 300 and standard tube may be by means of a screw system. The cavity applicator 300 may screw to a tube, adapter 350, or directly to a jar dispenser 400 that would have the proper mating system configured. Once the cavity applicator 300 is connected, then the larger container fills the smaller container. As the cavity applicator 300 gets filled, the plunger 10 rises, consistent with the cream or gel is inside the barrel 20 and corresponding to the dosage displayed on the plunger 10. Alternatively, in separate embodiment as seen in FIG. 22B, the cavity applicator 300 mates with the adapter 350 via a slide in and slide out connecting mechanism. Similarly, in a separate embodiment, FIG. 22A shows the mating between the adapter 350 and the cavity applicator 300 being a slide and snap connecting mechanism. The added snap mechanism facilitates a tighter fit when necessary. Lastly, on a separate embodiment, FIG. 29 and FIG. 30 show similar connecting mechanisms as described above, but the adapter 700 further comprises a flip cap to retard evaporation. The slide and snap mechanism would mate the applicator to the tube, jar, or metered dispenser. The proper amount of pressure would simply maintain the two parts attached.

Adapters—Dispenser Jar—Cavity Applicator

In the embodiments described below, the adapter has been configured to slide, snap, or screw to the lid of larger containers and dispensing jars to enable the transferring of flowable compositions into the small chamber of cavity dispensers. Furthermore, the adapter may feature semi-threaded characteristics to avoid the unscrewing process of the molded parts. Lastly, the adapter is configured to house a cap or flip cap on its distal end to retard evaporation of the contents inside the dispensing jar. With references to the embodiments as shown on FIG. 26, the user presses on the piston 285 of the jar dispenser 400 from the bottom with a thin rod or fingers, and the cream or gel preparation exits the chamber of the dispenser jar 400 through the center outlet 276 of the removable lid 275 and it continues its path through the inner chamber 244 of the adapter 350, and then it enters the inner chamber 111 of the cavity applicator 300. One notable advantage of this assembly, is the ability for the user to transfer the flowable preparation back into the dispenser jar 400 if desired; especially on cases where a larger than needed dosage was transferred into the applicator 300 by mistake.

Figure 31:
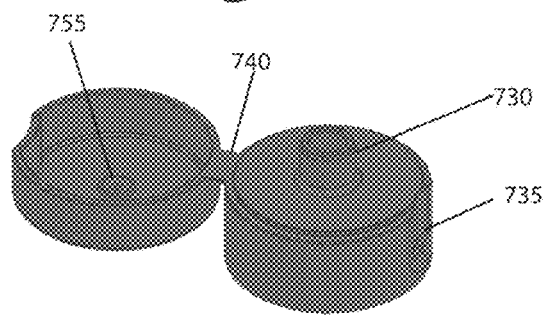
FIG. 31 is a top side view of the flip cap adapter.
Figure 32:
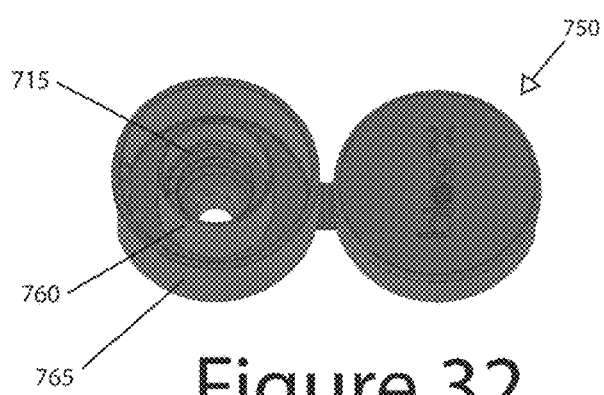
FIG. 32 is a top side view of an inverted flip cap adapter.

Alternatively, the embodiments of FIGS. 12 through 15 describe the adapter 350 which facilitates the connection of the jar dispenser 400 to the cavity applicator 300 where the outlet of the adapter 255 connects to the cavity applicator's barrel 20 by screwing the threaded end 170 of the barrel 20 with the threaded screw of the adapter 240. In a preferred embodiment, the outlet 255 of the adapter 350 connects to the barrel 20 of the cavity applicator 300 by sliding the top outer side wall 241 of the adapter 350 into the inner wall 185 of proximal end 21 of the barrel 20. Furthermore, at the proximal end 27 of the adapter 350 lies the internal threaded cavity 265 of the said adapter 350 which screws to the threaded outlet 295 of the removable lid 275 which is screwed to the jar dispenser 400 as seen on FIGS. 17 and 19. Similarly, on a separate embodiment as shown on FIGS. 31 and 32, the internal threaded cavity 715 is shown with a longer inner rim 760 around it. Also, a thumb indent 735 is evident, stemming from the outer wall of the outer side rim 765.

Figure 17:
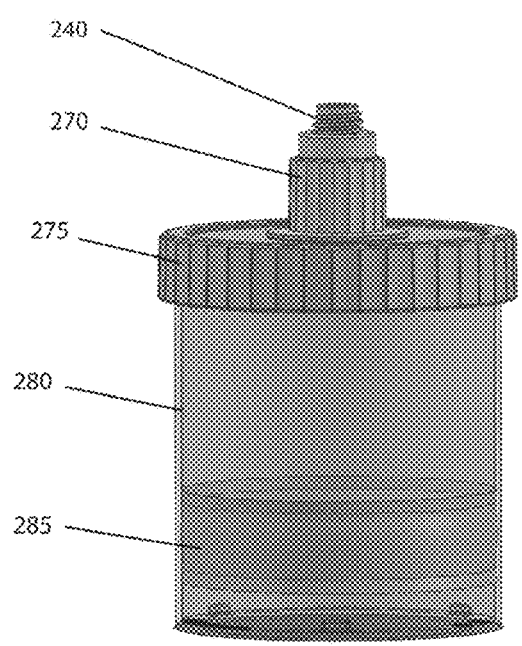
FIG. 17 is a side view of the jar with piston, barrel, screwable lid, and the screwable adapter attached.
Figure 18:
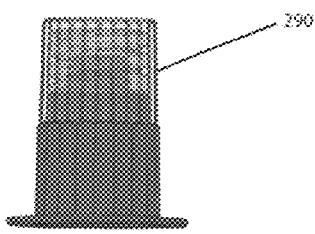
FIG. 18 depicts side view of the screwable adapter and screwable cap; although the cap is threaded on the inside, the external attachment to the cap takes place through slide-in, slide-off mechanisms.
Figure 19:
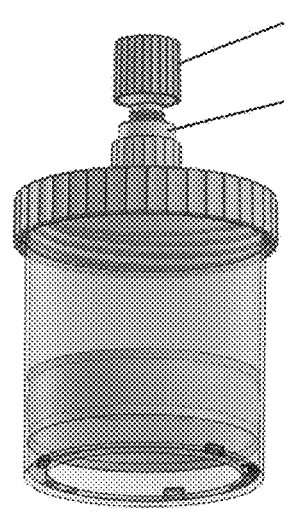
FIG. 19 depicts a side view of the barrel, piston, and screwable lid with a central outlet, screwable adapter, and cap.

Therefore, when the consumer exercises pressure on the piston 285 of the jar dispenser 400, as shown in FIGS. 17, and 19 the piston 285 travels and the contents inside the jar dispenser 400 exit through outlet 276 of the lid 275 and continue to travel through the inner chamber 244 of the adapter 350 into the inner chamber 111 of the barrel 20. As result, the plunger 10 attached to the barrel 20 of the cavity applicator 300 rises as the chamber 111 of the applicator 300 gets filled with the cream or gel preparation. If too much cream gets transferred, the consumer simply measures the correct amount with the dosing tabs 110 of the plunger 10 and presses the desired dosage. The cream or gel preparation travels back to the jar dispenser 400. In addition, any excess may also be discarded if desired. Once the desired dosage has been measured with the dosing tabs 110 of the plunger 10, the consumer detaches the cavity applicator 300, and inserts it into the cavity to the desired depth. The consumer presses the digit trigger 100 of the plunger 10 all the way down to apply the total measured amount of pharmaceutical preparation.

Figure 26:
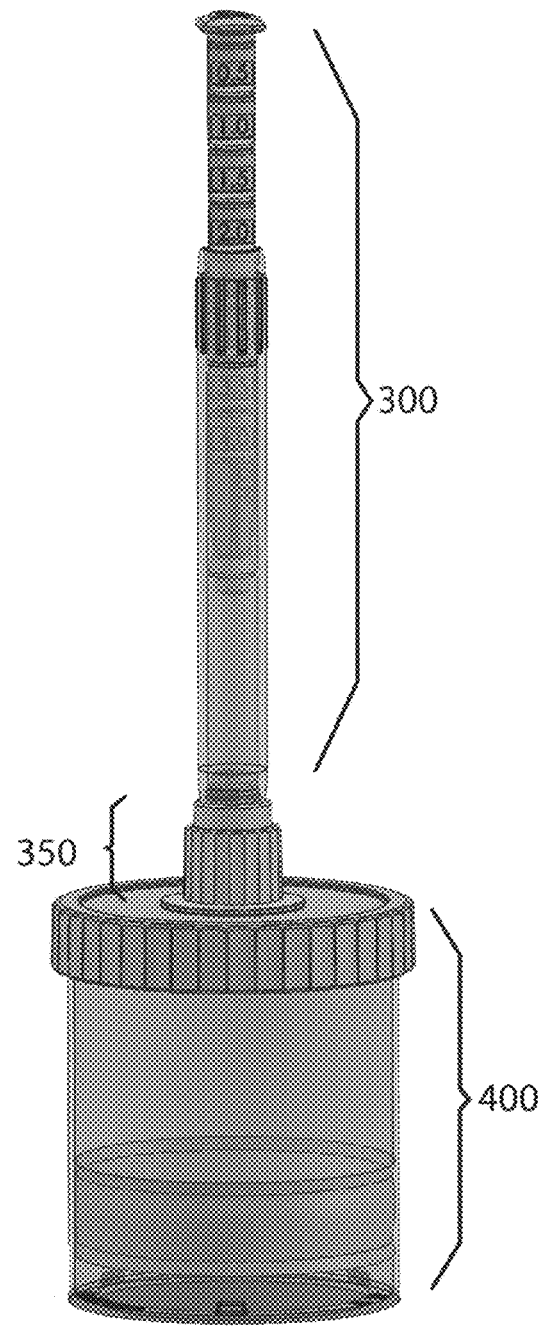
FIG. 26 is a side view of the jar dispenser, adapter, and cavity applicator.

In the embodiment as shown on FIGS. 22B and 26, the jar dispenser 400 has the ability of being connected to the cavity applicator 300 by means of the adapter 350 as previously mentioned. Likewise, on a separate embodiment, FIGS. 29 through 32 displays the jar dispenser 400 connected to the cavity applicator 300 by means of a flip-cap adapter 700. This adapter is similar to the adapter of FIGS. 13 through 15, 22B, and 26; but, it is configured with a flip cap to retard evaporation and to make it easier to access the inner contents. Furthermore, this flip cap adapter 700 also connects to the cavity applicator 300 by means of slide, snap, or screw mechanisms as previously demonstrated.

The barrel 20 of the cavity applicator 300 slides over the rim outlet 730 of the flip cap 700 and connects snugly. When the piston 285 of the jar dispenser 400 is pushed upwards towards its distal end, the flowable composition passes through the inner chamber of the flip cap adapter 700, and continues into the inner chamber 111 of the cavity applicator 300.

Figure 27:
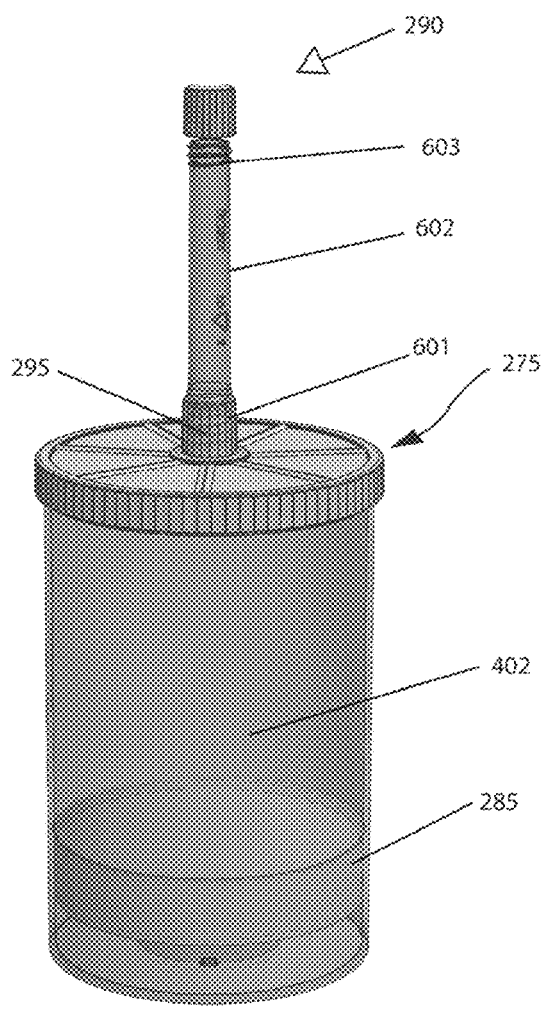
FIG. 27 is a side view of the dispenser jar, nozzle, and cap.
Figure 28:
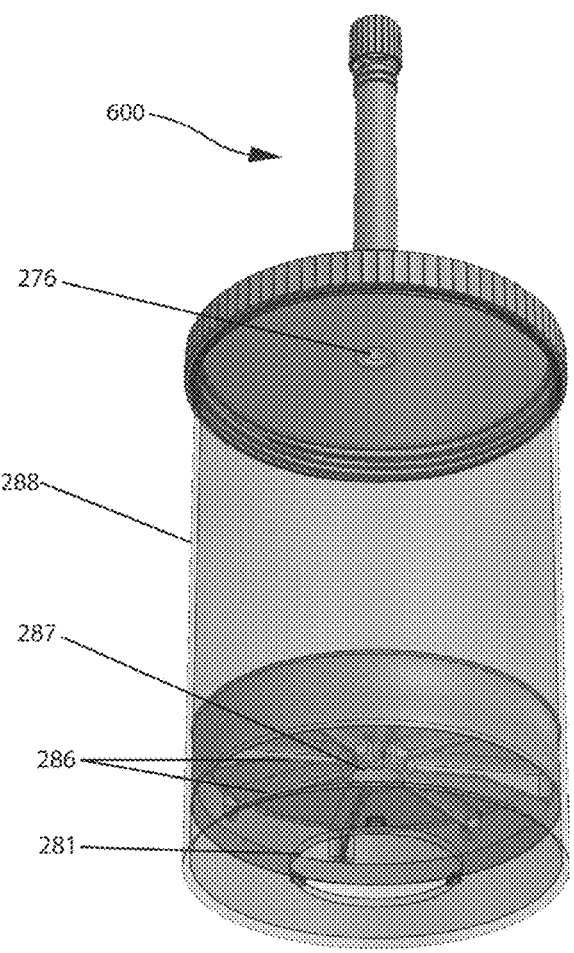
FIG. 28 is a bottom side view of the dispenser jar, nozzle, and cap.

On a separate embodiment, FIG. 27-28 exhibits a much larger dispenser jar 400. These dispenser jars 400 are generally configured for automated transfers, and a removable nozzle 600 is generally attached to facilitate the transfer from the larger dispenser jar (FIG. 27-28) into smaller jars and like containers.

Metered Dial Dispenser (Ticker and Cavity Applicator)

Figure 20A:
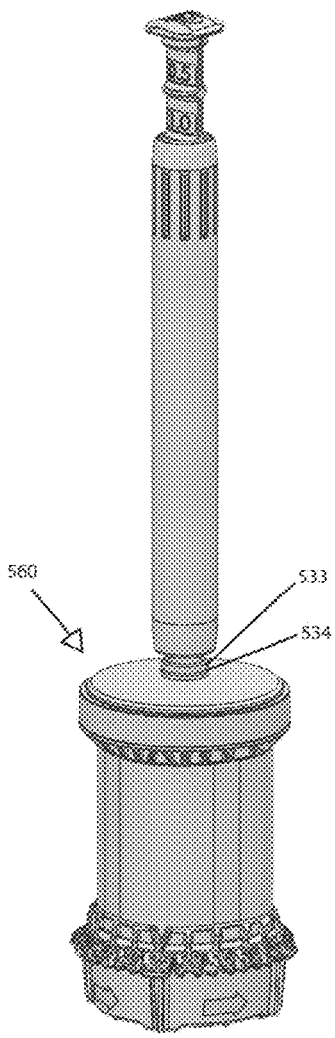
FIG. 20A is a side view of the bi-audible, bi-tactile, visual metered-dose applicator with the barrel and plunger of the cavity applicator right above it; the connection configured in this illustration is via a combined slide and snap mechanism.
Figure 20B:
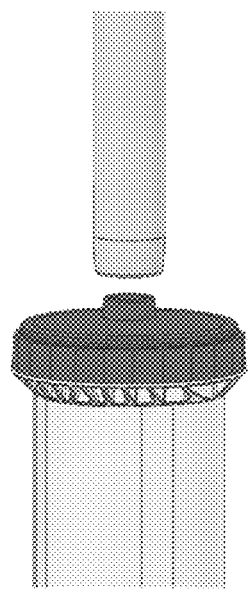
FIG. 20B is a side view of the bi-audible, bi-tactile, visual metered-dose applicator with the barrel and plunger of the cavity applicator right above it; the connection configured in this illustration is solely via a slide mechanism.

FIGS. 20A, 20B, and 23 through 25 refer to the bi-audible, bi-tactile, and visual applicator described in U.S. Pat. No. 8,544,684 (to which priority is claimed) with further modifications to its dispenser lid 560 to accommodate the attachment of a cavity applicator through slip, snap, screw, or a combination of more than one connecting mechanism. Furthermore, the dispenser lid 560 of the metered dial dispenser 500 can also be configured to mate with a silicon, rubber, or other soft material adapters to assist in the application to sensitive body areas of humans or animals. FIG. 20A is a side view of the metered dial-dispenser 500 attached to a cavity applicator 300 by combined means of Slip-On and Slip-Off and Snap-On and Snap-Off connecting mechanisms. However, the cavity applicator 300 has capabilities of being fully attached to the metered dial-dispenser 500 solely through its slip-on and slip-off mechanism as shown on FIG. 20B.

Figure 23:
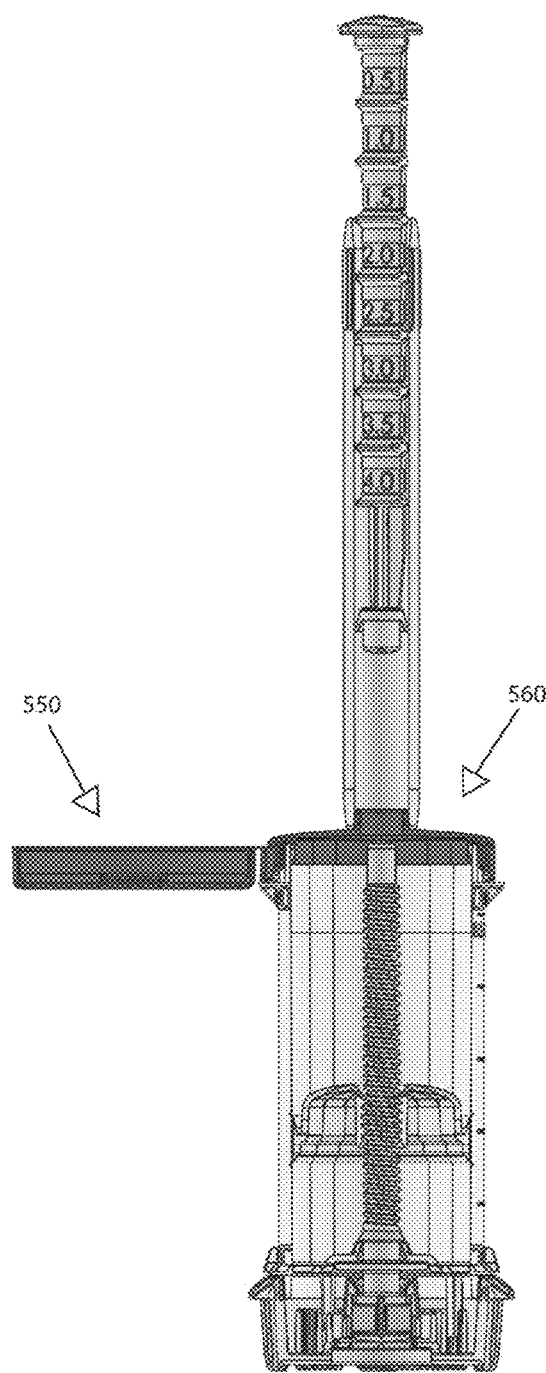
FIG. 23 is a cross-sectional side view of the bi-audible, bi-tactile, visual metered-dose applicator slipped into the barrel of the cavity applicator; a cross-section of the plunger is also shown as well as a flip cap.

Next, FIG. 23 is a cross-sectional, side view of the metered dial-dispenser displaying a flip cap 550 to retard evaporation and the dispenser lid 560 configured to mate with the cavity applicator 300 through a collaborative slip and snap connecting mechanism. In this embodiment, the proximal end 21 of the barrel 20 of the cavity applicator 300 slips in through the external wall of the outlet 533 and then it snaps-onto place by means of the outlet rim 534 of the dispenser lid 560 of the metered dispenser 500, connecting to an optional rim indent 174 of the cavity applicator 300 to cause an even tighter connectivity.

Figure 24:
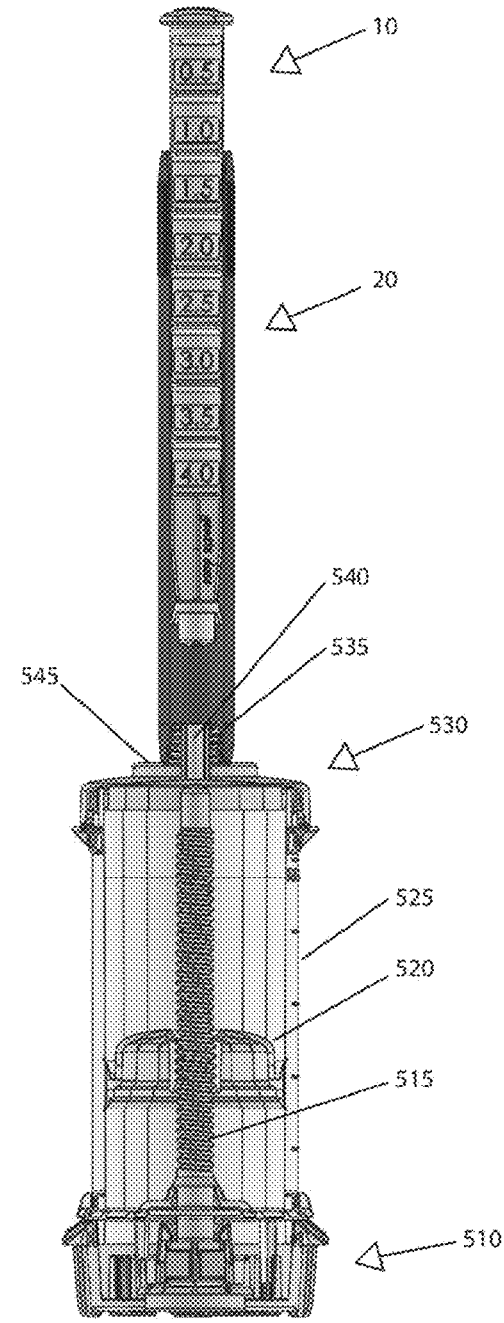
FIG. 24 is a cross-sectional side view of the bi-audible, bi-tactile, visual metered-dose applicator screwed to the barrel of the cavity applicator; a cross section of the plunger is also shown.
Figure 25:
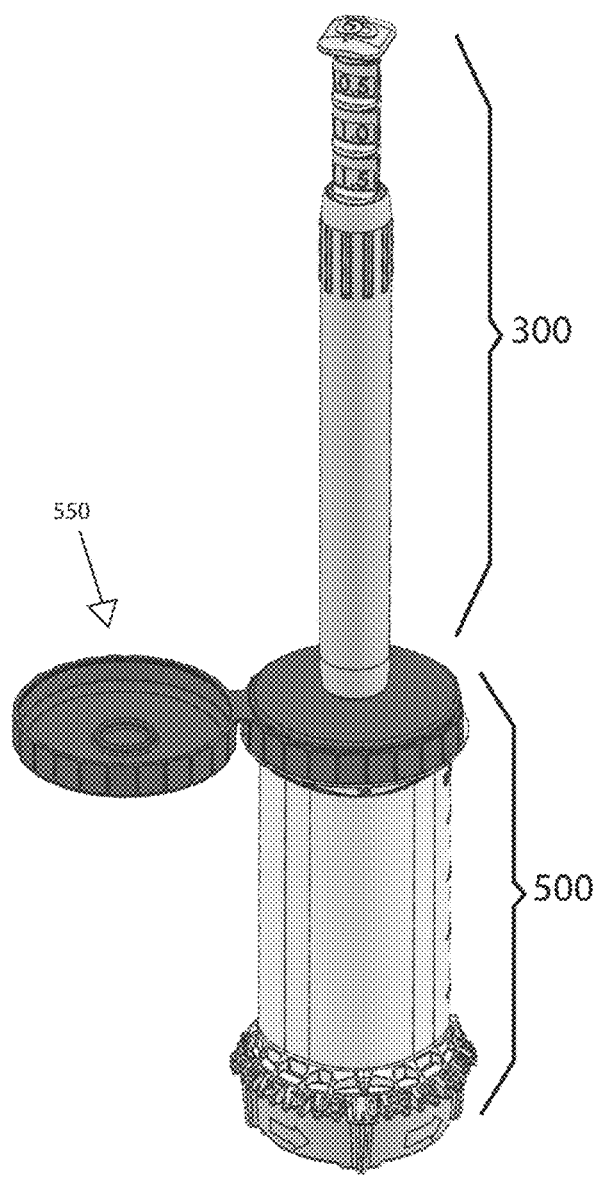
FIG. 25 is a top side view of the bi-audible, bi-tactile, and visual metered-dose applicator connected to the barrel of the cavity applicator; as the dial of the metered-dose applicator rotates clockwise by 30 clicks (540 degrees), an internal piston rises and the flowable composition gets transferred to the chamber of the cavity applicator; the plunger on top of the barrel is set to deliver a 1.5 gram volumetric dosage of flowable pharmaceutical composition.

In a separate embodiment, FIG. 24 is a cross-sectional, side view of the metered dial-dispenser screwed to a cavity dispenser. As described in U.S. Pat. No. 8,544,684, the base 510 of the metered dial-dispenser is coupled the screw 515. Clockwise rotation of the base 510 causes the screw to rotate which drives the piston 520 upwards. Contents inside the chamber of the barrel 525 exit through the outlet 540 of the dispenser lid 530. Furthermore, the threaded outlet 535 of the dispenser lid 560 connects to the proximal threaded end 170 of the barrel 20 of the cavity applicator 300. As the flowable contents enter the inner chamber of the cavity applicator, the plunger rises and the dosing interval 140 is consistent with the axial displacement of the base of the metered dial-dispenser. In other words, five clicks of the base 510 of the metered dial-dispenser 500 correspond to a 90 degree axial rotation, which, also correspond to a ¼ milliliter of flowable cream or gel preparations being transferred to the chamber of the cavity applicator 300. The end user then unscrews the cavity applicator 300, then applies the medicament as instructed.

In various embodiments as described herein, example embodiments include at least the following examples.

An adapter comprising: an outlet for a flowable pharmaceutical composition to exit or to be transferred to a secondary chamber; an inner chamber formed when the adapter is connected to two independent dispensing systems; an internal threaded or semi-threaded area on a proximal end of the adapter; an unthreaded or threaded area spanning around a distal and medial external circumference; a grip area spanning around a proximal external circumference; and a cap or flip-cap to provide closure at a distal end to prevent evaporation of the flowable pharmaceutical composition.

The adapter as claimed above, being configured to connect to a cavity applicator on the distal end through a screw, slide, snap, or a combination of connecting mechanisms.

The adapter as claimed above, being configured to connect to ajar dispenser on the proximal end through a screw, slide, snap, or a combination of connecting mechanisms.

The adapter as claimed above, being configured to facilitate a transfer of cream and gel pharmaceutical preparations from larger dispensing jars into smaller containers.

The adapter as claimed above, being configured with a removable cap or flip-cap to retard evaporation a flowable semi-liquid pharmaceutical composition.

A metered dial-dispenser comprising: a cap to retard evaporation; a lid with a central outlet; a center screw; a piston; a body; and a rotatable base with a plurality of dial tabs spanning around its outer circumference.

The metered dial-dispenser as claimed above further including a dispenser lid configured to connect to a cavity applicator through a slide, snap, screw, or a combination of connecting mechanisms.

The metered dial-dispenser as claimed above further including a dispenser lid configured to mate with a removable adapter made of silicon, rubber, or other soft, elastomeric material to assist in application to sensitive body areas or cavities in humans and animals.

The metered dial-dispenser as claimed above wherein the removable cap being configured as a slide cap, snap cap, screw cap, or flip cap to retard evaporation and to facilitate connectivity.

The metered dial-dispenser as claimed above being configured for automated or manual loading from a larger container.

A non-metered cylindrical jar dispenser for dispensing or transferring flowable contents, the jar dispenser comprising: a removable cap to retard evaporation; a removable nozzle for dispensing contents including a flowable pharmaceutical composition; a removable lid with a central outlet to contain the contents; a barrel to house an inner chamber; and a removable piston for driving the contents.

The jar dispenser as claimed above configured to screw to an adapter.

The jar dispenser as claimed above, wherein the removable nozzle is configured for transferring flowable pharmaceutical composition.

The jar dispenser as claimed above being configured for automated or manual driving of the piston to dispense different volumetric dosages of flowable pharmaceutical composition through the central outlet and the removable nozzle.

The jar dispenser as claimed above configured with a threaded or unthreaded cap.

The jar dispenser as claimed above configured with a removable lid comprising a central outlet at its distal end that is externally threaded, a removable cap being configured as a screw-in cap to retard evaporation.

The jar dispenser as claimed above configured with a removable lid comprising a central outlet at its distal end that is externally unthreaded, a removable cap being configured as a slide-in cap to retard evaporation.

The jar dispenser as claimed above being configured to connect to a cavity applicator by means of an adapter.

The jar dispenser as claimed above configured to connect directly to a cavity applicator.

The jar dispenser as claimed above, the cavity applicator as claimed above, the metered dial-dispenser as claimed above, and the adapter as claimed above preferably made of an elastomeric or semi-elastomeric material.

A method of dispensing comprising: filling a dispenser jar with a flowable composition; securing a dispenser lid; screwing a nozzle to the dispenser lid; and pressing a piston of the dispenser jar to transfer the composition to other containers, cavities, or applicators.

The method as claimed above wherein the dispenser jar includes a piston at a proximal end, a barrel, a removable screw-on lid at a distal end with a central outlet, a nozzle, and a removable screw-on cap.

The method as claimed above, wherein the flowable composition is a flowable pharmaceutical composition of a type from the group consisting of: a gel, cream, lotion, and an ointment.

The method as claimed above further including pressing the piston with a manual or automated rod to transfer the flowable composition from the dispensing jar with accuracy and precision into smaller containers or cavity applicators.

The illustrations of embodiments described herein are intended to provide a general understanding of the structure of various embodiments, and they are not intended to serve as a complete description of all the elements and features of components and systems that might make use of the structures described herein. Many other embodiments will be apparent to those of ordinary skill in the art upon reviewing the description provided herein. Other embodiments may be utilized and derived, such that structural and logical substitutions and changes may be made without departing from the scope of this disclosure. The figures herein are merely representational and may not be drawn to scale. Certain proportions thereof may be exaggerated, while others may be minimized. Accordingly, the specification and drawings are to be regarded in an illustrative rather than a restrictive sense.

The description herein may include terms, such as "up", "down", "upper", "lower", "first", "second", etc. that are used for descriptive purposes only and are not to be construed as limiting. The elements, materials, geometries, dimensions, and sequence of operations may all be varied to suit particular applications. Parts of some embodiments may be included in, or substituted for, those of other embodiments. While the foregoing examples of dimensions and ranges are considered typical, the various embodiments are not limited to such dimensions or ranges.

The Abstract is provided to allow the reader to quickly ascertain the nature and gist of the technical disclosure. The Abstract is submitted with the understanding that it will not be used to interpret or limit the scope or meaning of the claims.

In the foregoing Detailed Description, various features are grouped together in a single embodiment for the purpose of streamlining the disclosure. This method of disclosure is not to be interpreted as reflecting an intention that the claimed embodiments have more features than are expressly recited in each claim. Thus, the following claims are hereby incorporated into the Detailed Description, with each claim standing on its own as a separate embodiment.

As described herein, example embodiments relate to an applicator for inserting flowable pharmaceutical preparations into a body cavity, an adapter for connecting a jar to a cavity dispenser, a jar dispenser with a nozzle for automated transferring and dispensing of flowable pharmaceutical compositions, and a metered dial-dispenser configured to connect to a cavity dispenser for humans and animals. Although the disclosed subject matter has been described with reference to several example embodiments, it may be understood that the words that have been used are words of description and illustration, rather than words of limitation. Changes may be made within the purview of the appended claims, as presently stated and as amended, without departing from the scope and spirit of the disclosed subject matter in all its aspects. Although the disclosed subject matter has been described with reference to particular means, materials, and embodiments, the disclosed subject matter is not intended to be limited to the particulars disclosed; rather, the subject matter extends to all functionally equivalent structures, methods, and uses such as are within the scope of the appended claims.

In various embodiments, a transdermal, visual, hi-audible and bi-tactile to the senses cream applicator with calibrated, equispaced line demarcations, and supplemental numerical legend, each positioned at a predetermined 18 degree angle from one another translating to the delivery of roughly a $\frac{1}{20}$th milliliter of flowable cream-base medicament of a specific density is described in detail herein. Additionally, a novel dosing protocol is described that utilizes a novel delivery system by which an elaborate set of instructions cause a combined continuous and variable topical composition dosing scheme of human identical progesterone and estradiol when self-administered by a user.

FIGS. 33-46 depict an embodiment of a dispensing apparatus 501 with regard to this novel system for the delivery of cream, gel, ointment, or any suitable flowable substance of interest.

This novel applicator 501 comprises the following six vital elements: a rotatable platform 2501, a house 47001, a screw-complex 20001 (see FIG. 40), an elevator 32501, a dispenser 50001, and a safety cap 60001.

All parts can be made of rigid plastic or a similar material, but the preferred material is polypropylene. Prototypes can be designed in ProJet, Stereolithography (SLA), or Acura 25.

FIGS. 33A and 33B introduce the assembled apparatus 501 as a complete unit (FIG. 33A) or as a vertical cross sectional view, (FIG. 33B) where the house 47001 is located in between the dispenser 50001 and the rotatable platform 2501. The elevator 32501 rests at the bottom of the inner chamber of the house 47001, where the left threaded screw-complex 20001, which is secured in between the house 47001 and the rotatable platform 2501 causes it to rise upon clockwise rotation of the rotatable platform 2501. A safety cap 60001 with a plug 63001 to retard evaporation and prevent contamination of the cream is situated on top of the dispenser 50001, where the safety cap 60001, which can snap into the dispenser end of the house 47001 by cooperation of the semi-annular rib 64501 on the inner wall of the safety cap 60001 and the safety rim 40801 on the outer wall of the dispenser end 40101 of the house 47001 adjacent to the upper rim 41501. The dispenser 50001 gets locked into the dispenser end 40101 of the house 47001 by interaction of the annular groove 54001 on its inner side wall 55001 and the peripheral rim 40701 on the outer wall of the dispensing end 40101 of the house 47001. An outer slim wall 55501 fits in between the elevator's outer side wall 31501 and the inner side wall 3501 of the house 47001. The elevator 32501 and screw shaft 24501 inside the house 47001 interact only to allow upward movement upon clockwise rotation of the rotatable platform 2501. The house locking tabs 42501 override the snap ring 21001 landing into the orbit area 24001 and locking the screw-complex 20001 in place only to allow axial movement. Platform locking tabs 14501 override the bolt-head 22001 and secure the bolt-neck 23501, thereby locking the rotatable platform 2501 in place. The strategic position of the bolt neck 23501, which, resides in between the joined washer 21501 and the bolt head 22001 serve to secure the platform locking tabs 14501 that stem from the bottom inner wall 10501 of the rotatable platform 2501 and consequently the rotatable platform 2501 as a whole to prevent movement to such segment in any direction. Once the rotatable platform 2501 is attached to the screw-complex 20001, the only possible movement, which involves the cooperation of the rotatable platform 2501 and the screw-complex 20001 behaving as a single unit, is to rotate clockwise around its own axis.

With the screw-complex 20001 set in place interacting with the rotatable platform 2501, house 47001, and elevator 32501, its mechanism can be fully appreciated. The primary ticker tabs 43501 interact with minor side ticks 11001 on the rotatable platform 2501, and produce a unique and identifiable sound depending on the displacement of the rotatable platform 2501 against the house 47001. Upon an 18° displacement, primary ticker tabs 43501 can clear the minor side ticks 11001 to land into tab rest segments 11101 and produce the second sound, or they can clear the major side ticks 11201 to land into different tab rest segments 11101 to produce the first sound. When the secondary ticker tabs 44001 clear the redundant side ticks 11501 upon an 18 degree rotation of the rotatable platform 2501, the first sound is also emitted by the apparatus and captured by the senses of the consumer. Therefore, primary ticker tabs 43501 interact with major side ticks 11201 concurrently when secondary ticker tabs 44001 interact with redundant side ticks 11001. Advantageously, there are only four major side ticks 11201 strategically positioned to interact with the primary ticker tabs 43501 and produce a louder identifiable sound only at key displacement locations; specifically at every 90°, 180°, 270°, and 360° displacement locations from a predetermined reference point; which also corresponds to the alignment of the 0.25, 0.50, 0.75, and 1.0 major digit tabs 7001 of the rotatable platform 2501 with the fixed major line markings 6501 of the house 47001.

In addition, at these four displacement locations, (90°, 180°, 270°, and 360°) there is sound summation taking place due to the concurrent interaction of primary ticker tabs 43501 with major side ticks 11201, as well as secondary ticker tabs 44001 interacting redundant side ticks 11501; ultimately yielding a more pronounced sound and tactile sensation at these predetermined sites.

FIG. 33C presents a horizontal cross-section of the lower end of an assembled apparatus emphasizing major 7001 and minor 6501 digit tabs. There are twenty digit tabs arranged in reverse ascending order along the equispaced digit zone 13301, and each digit tab is separated by an 18° angle from one another. The attachment of the rotatable platform 2501 with the housing 47001 creates the graduation area 8501; which is essential in allowing users to determine a specified volumetric dose. A cartoon arrow below the illustration 7501, points to the direction of allowed movement of the unidirectional rotatable platform 2501.

There are four grip tabs 3001 to ease rotation. Further, the lower end of the house 47001 provides equispaced extruded line demarcations to create a predetermined point of reference during rotation of the rotatable platform 2501. Fixed major markings 6501 and fixed minor markings 5001 span along the outer circumference of the lower end of the house 47001. An elevator 32501 residing inside the chamber of the house 47001 is attached to the screw shaft 24501 and causes it to rise upon clockwise rotation of the rotatable platform 2501.

Figure 34:
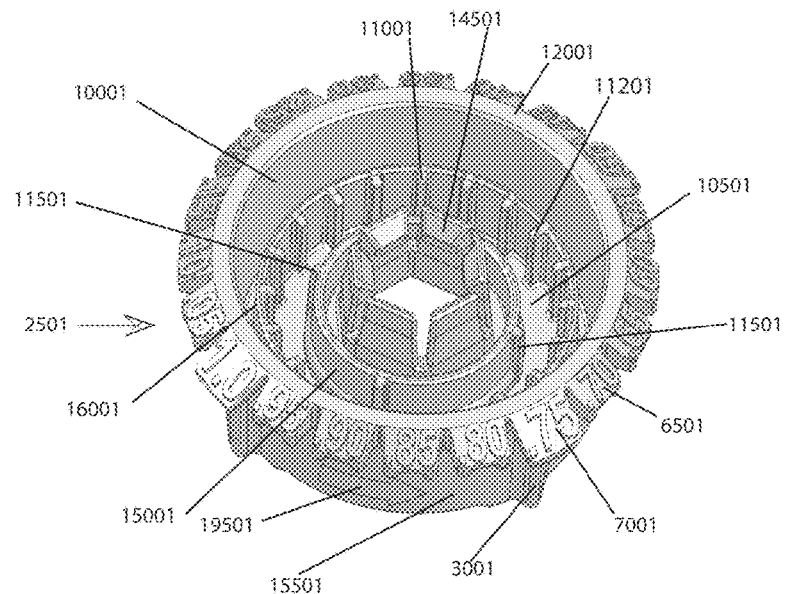
FIGS. 34, 35, and 36 are schematic views of the rotatable platform.
Figure 35:
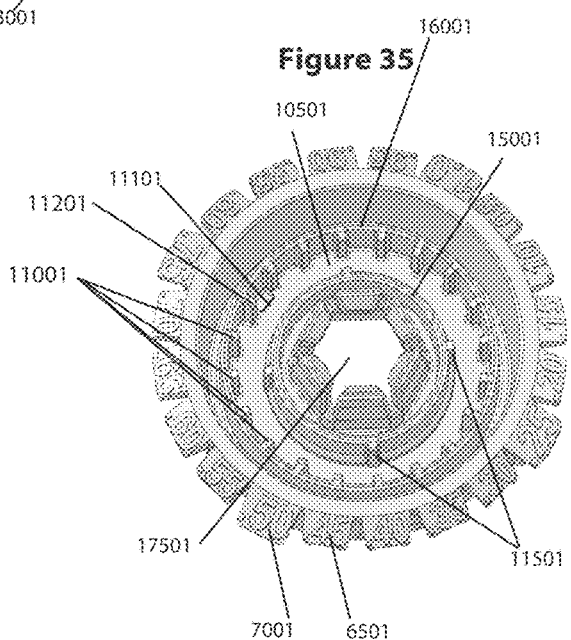
Figure 36:
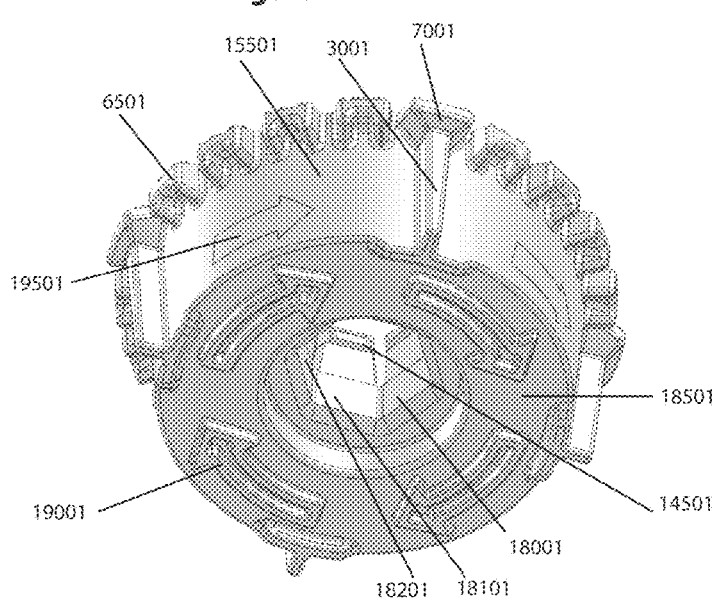
Figure 37A:
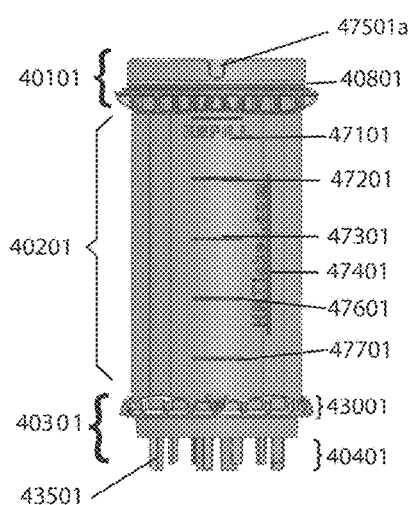
FIGS. 37A, 37B, 38, and 39 exhibit different schematic views of the house.
Figure 37B:
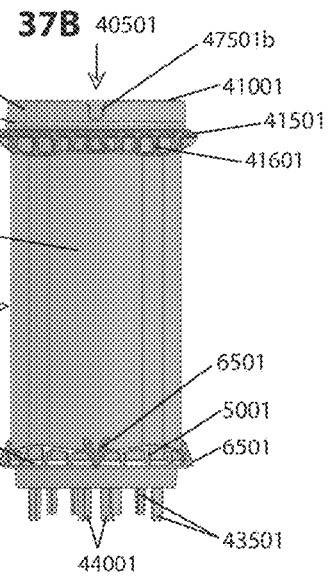
Figure 38:
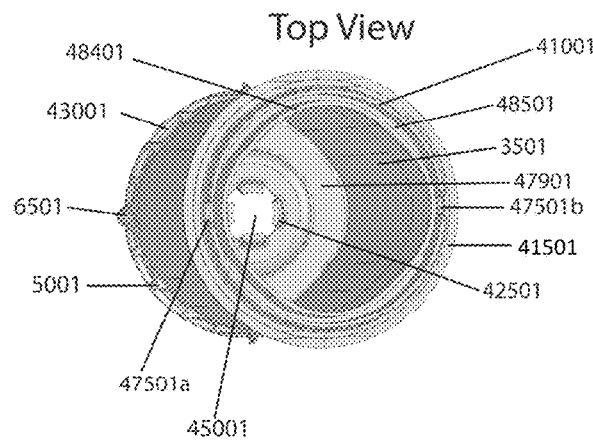
Figure 39:
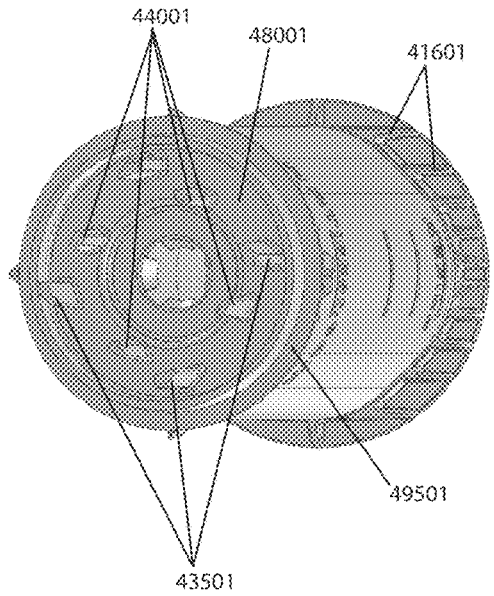

FIGS. 34-36 are schematic views of the rotatable platform 2501, where the outer side wall 15501 of the rotatable platform houses the equispaced digit zone 13301 which comprises four raised major digit tabs 7001, and sixteen raised minor digit tabs 6501 all arranged in ascending order (by 0.05 intervals) as the platform 2501 rotates clockwise against the house 47001. In addition, the platform outer side wall 15501 has four side grips 3001; each situated right below each major digit tab 7001 (positioned at 90° degrees from each other along the outer circumference) which span along the equispaced digit zone 13301 to facilitate rotation of the platform 2501. The platform lip 12001 makes contact with the graduated ring base 49501 of the house 47001 to create the graduation area 8501, (FIG. 33A). FIG. 36 presents the bottom end of the rotatable platform 2501 where side arrows 19501 and bottom arrows 19001 indicate the direction of movement allowed by the rotatable platform 2501.

FIG. 34 and FIG. 36 are schematic views of the rotatable platform 2501 where locking tabs 14501 extend upward from the center of the bottom inner wall 10501, having six slanted but downward pointing locking tabs 14501 which serve to override the bolt head 22001 and land onto the bolt neck 23501 practically fusing the screw-complex and rotatable platform 2501 as one piece. The rotatable platform 2501 outer base rim 16001 houses sixteen minor side ticks 11001 and four major side ticks 11201; which interact with ticker tabs stemming from the bottom exterior wall 48001 of the house 47001. Additionally, four redundant side ticks 11501 equispaced from one another stem from the inner base rim 15001 of the platform 2501 to engage with four secondary ticker tabs 44001 also stemming from the outer bottom exterior wall 48001 of the house 47001. The inner side wall 10001 of the rotatable platform 2501 could potentially house major and minor side ticks as well in lieu of the outer base rim 16001.

FIG. 36 presents another schematic view the rotatable platform 2501 where the bottom exterior wall 18501 of the rotatable platform 2501 is clearly exhibited. The locking tabs 14501 point inward towards the bottom of the hexagon void 17501. There is one locking tab 14501 stemming from each upper corner of the hexagon side wall 18001, 18101, 18201, where the two walls join. Further, bottom indication arrows 19001, and side indication arrows 19501 show the direction of allowed movement of the rotatable platform 2501.

The house 47001, which is basically a barrel, is introduced in FIGS. 37A-39, having three major sections. A dispenser end 40101, a body 40201, and a platform end 40301 comprising a graduation ring 43001 and a clicking zone 40401. The body 40201 of the house 47001 consists primarily of an inner side wall 3501, and the outer side wall 4001, which, can accommodate a label with consumer instructions. At the dispenser end 40101, there is a dispenser opening 40501 used to load the cream-base medicament into the chamber of the house 47001. There are two dispenser notches 47501a, 47501b at opposite ends of the circular upper edge 41001, which guide the insertion guides 53001 of the dispenser 50001 to properly slip in upon pressing against the house 47001. A peripheral rim 40701 on the house outer side wall 4001 engages with its complementary annular groove 54001 on the inner side wall 55001 of the dispenser 50001 locking it upon pressing against the house 47001.

An extruded upper rim 41501 with reinforcement ribs 41601 just beneath it is situated just below the circular upper edge 41001 which assists in locking the dispenser 50001 upon pressing against it. The inner side wall 3501 of the house 47001 is directly in contact with the composition and it is perpendicular to the bottom inner wall 47901; which, on its center has a void with four upward projecting locking tabs 42501 for accepting and locking the screw-complex 20001 in place with the house 47001 only to allow rotation along its own axis. The chamber upper edge 48401 concludes the upper end of the chamber; which has a semi-square shape in order to maximize volume, but it is connected to the circular upper wall 40601 by a wall to wall connector 48501, that terminates at the top with the circular upper edge 41001.

The platform end 40301 of the house 47001 has a raised graduation ring 43001, with twenty demarcation line markings, referred here as fixed major and minor line markings (6501; 5001); respectively. There are four fixed major line markings 6501, separated at 90° from each other along the outer circumference of the of platform end 40301 of the house 47001 and sixteen fixed minor line markings 5001, all forming the graduation ring 43001. The primary ticker tabs 43501 stemming from the platform end 40301 of the house interact with minor side ticks 11001 stemming from the outer base rim 16001 of the rotatable platform 2501 producing a unique but soft second sound at every 18° of rotation depending on the angular displacement from a predetermined point of reference. In addition, the primary ticker tabs 43501 also interact with major side ticks 11201 stemming from the outer base rim 16001 of the rotatable platform 2501 to produce a louder first sound upon clearance of the primary ticker tabs 43501. The secondary ticker tabs 44001 interact with the redundant side ticks 11501 of the rotatable platform 2501 to produce the louder first sound upon completion of an 18° movement by the platform to any major digit tab 7001 position, (or a 90° predetermined angular displacement from a fixed point of reference) as well as a specific vibration that corresponds to the tactile component that users can sense. Furthermore, an even louder sound and greater tactile sensation is achieved by summation of ticker tabs to side tick interactions; specifically, primary and secondary ticker tabs interacting with major and redundant side ticks, simultaneously, where the landing of all ticker tabs take place upon completion of an 18° displacement into the major digit tabs 7001. A screw orifice 45001, accepts the screw-complex 20001 and the locking tabs 42501 override the snap ring 21001 landing into the orbit area 24001 of the screw-complex 20001 where the screw-complex 20001 is practically locked to the house 47001.

Figure 40:
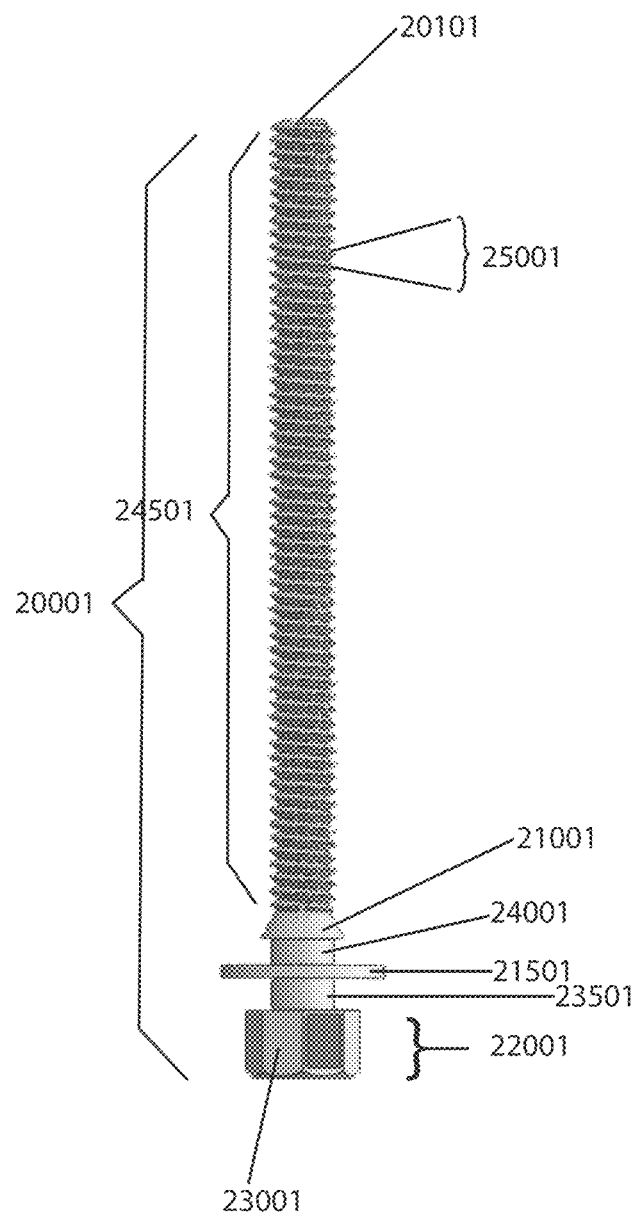
FIG. 40 is a side view of the screw-complex comprising a head bolt, joined washer, snap ring, and screw.

FIG. 40 illustrates the bolt head 22001, joined washer 21501, snap ring 21001, and a screw 24501. Once combined, all these components form the screw-complex 20001. The pitch 25001 is the distance between threads; which, causes a predetermined but specific elevation on the elevator; ultimately having a role on dosing. The screw end 20101 of the screw-complex 20001 continues downward along the screw 24501 until the threading stops at a snap ring 21001; which, upon passing, it secures the screw-complex 20001 to the house 47001 cooperating with four upward slanted locking tabs 42501 stemming from the bottom inner wall 47901 of the house 47001 and a joined washer 21501 that serves as a securing mechanism. The bolt head 22001 has six equal head side walls 23001. The bolt neck 23501 is the area between the bolt head 22001 and joined washer 21501; which serves to secure the rotatable platform 2501.

Figure 41:
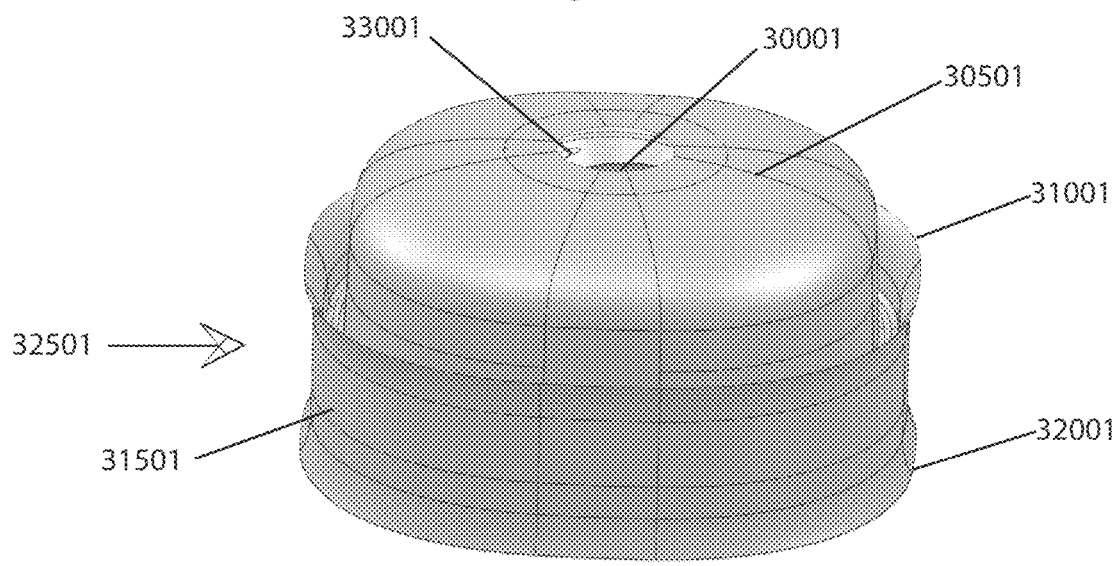
FIGS. 41 and 42 present 3-dimensional views of the elevator displaying a top and a bottom edge seal, a top outer wall, a female threaded ring, and a center void.
Figure 42:
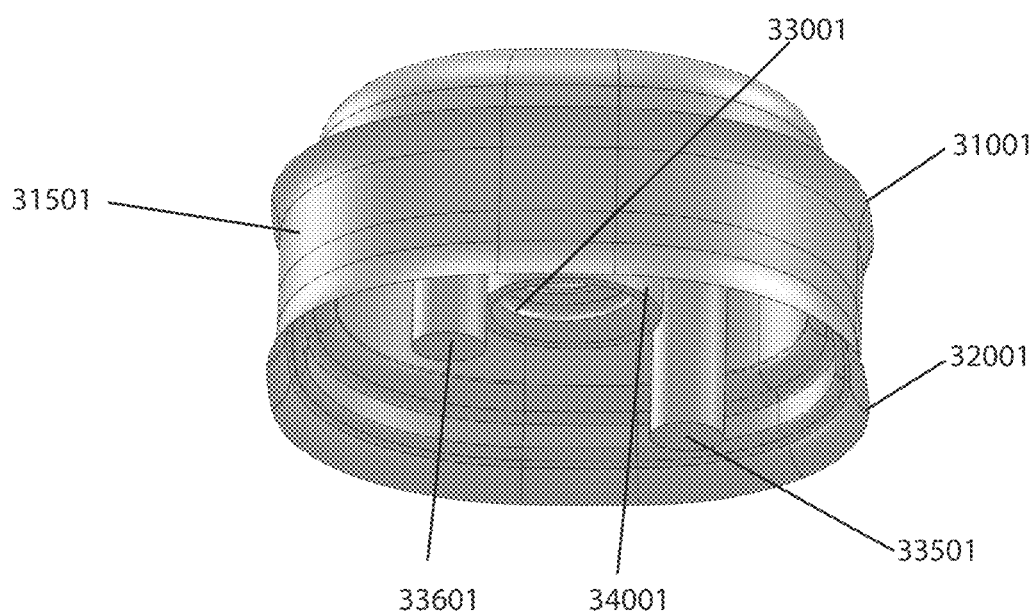

FIG. 41 is a schematic view of the elevator 32501. The elevator pushes the cream-base medicament, which resides in a closed chamber upwards, to exit through an outlet 50501 upon movement of the rotatable platform 2501. The top outer wall 30501 is dome shaped with a concave outer side wall 31501 where the top edge seal 31001 and bottom edge seal 32001 are at opposite ends; which, also serves to prevent cream form smudging or being left behind. On the center of the elevator 32501, there is a ring void 30001 that interacts with the treaded area of the screw 24501. The bottom view of the elevator 32501 is presented on FIG. 42 where the female threaded ring 33001 appears around the center of the elevator 32501, as well as the intrinsic wall 34001 where it stems from. There are two assembly stoppers 33501, 33601 to prevent damage to the elevator by the assembly tooling.

Figure 43:
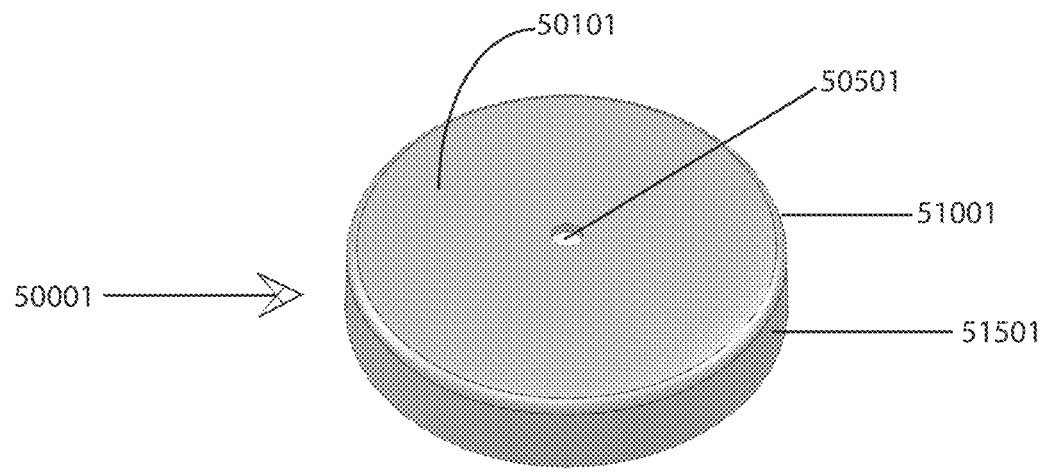
FIGS. 43 and 44 depict two perspective views of an isolated dispenser with the top and bottom views exposed.
Figure 44:
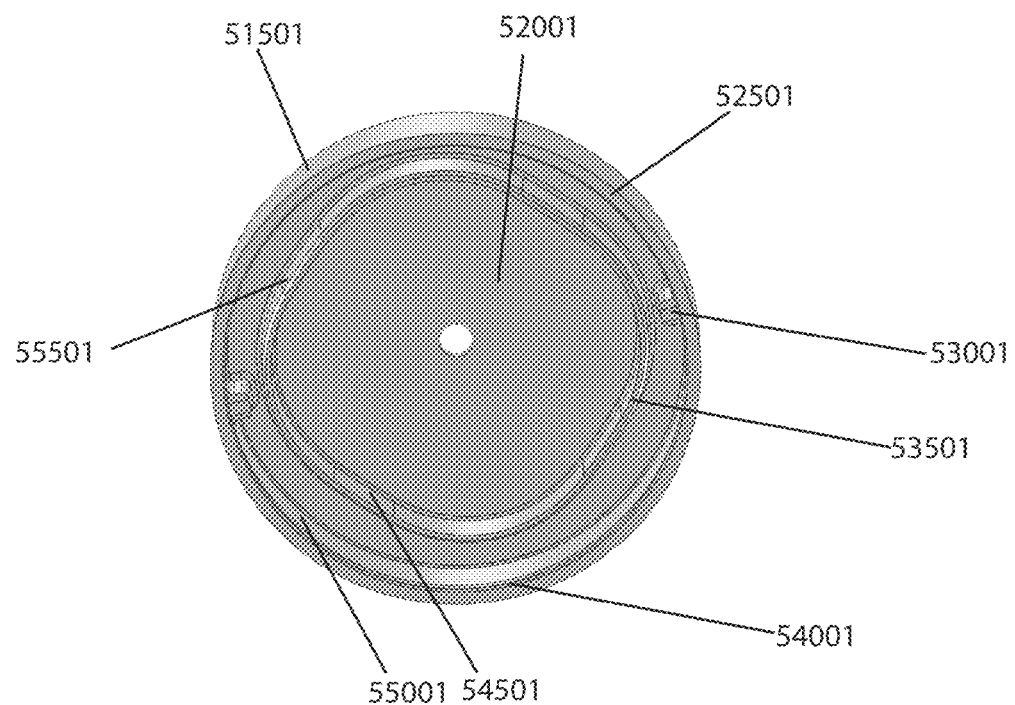

FIG. 43 is a schematic view of the dispenser 50001 where the dispensing pad 50101 serves as a dispensing element. The outlet 50501 allows the cream-base medicament to be expelled and perhaps temporarily reside there until application. The smooth upper edge 51001 connects the outer side wall 51501 and dispensing pad 50101 together. FIG. 44 is a schematic view of the dispenser 50001, where the bottom side of the dispenser is exposed, causing the following to appear; the top inner wall 52001, the inner side wall 55001, and a dispenser bottom edge 52501. An additional wall exists to seal the cream inside the chamber and prevent dispersion. It consists of an inner slim wall 54501, an outer slim wall 55501, and the slim edge 53501. There are two insertion guides 53001 on the inner side wall 55001 at opposite positions along the circumference to fit into the dispenser notch 47501a, 47501b allowing the dispenser to slip onto the dispenser end 40101 of the house 47001. The dispenser 50001 snaps tightly into the house 47001 and cannot be detached by cooperation of the annular groove 54001 and the peripheral rim 40701 of the house 47001.

Figure 45:
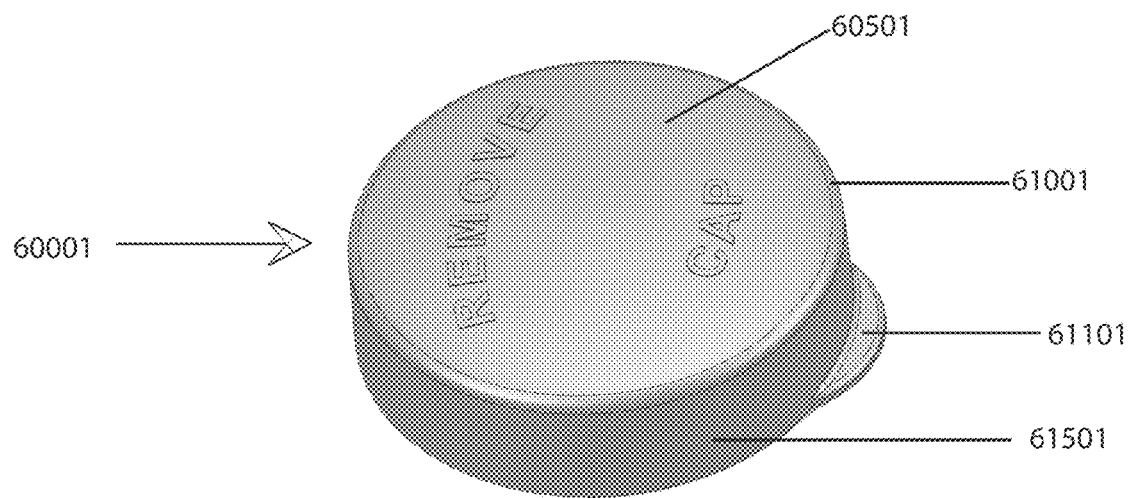
FIGS. 45 and 46 present two perspective views of the safety cap suspended in mid-air.
Figure 46:
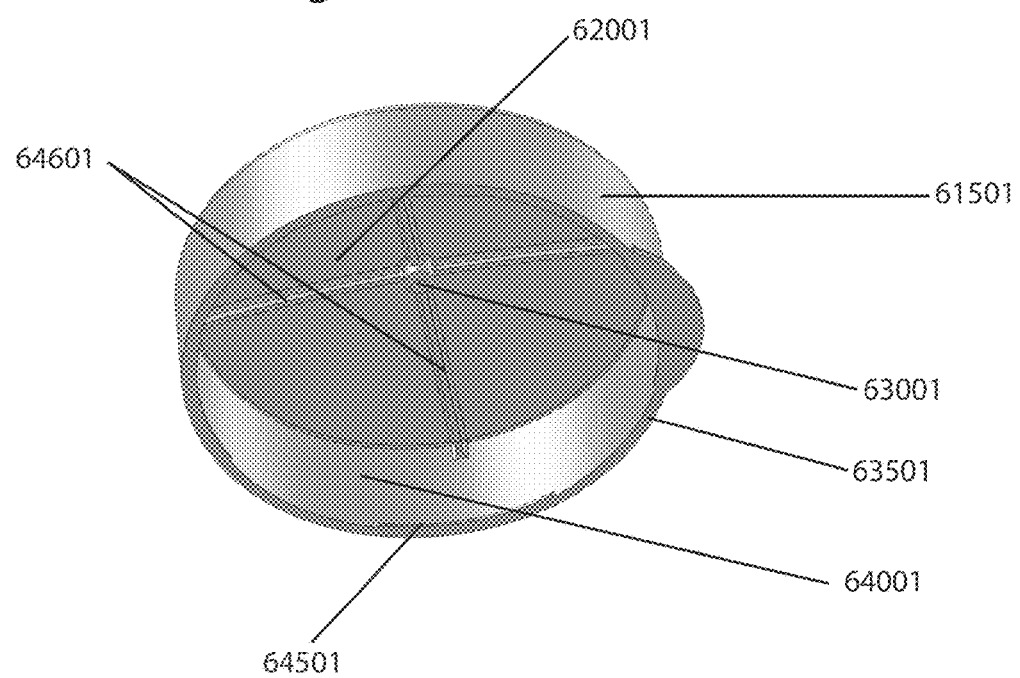
Figure 47:
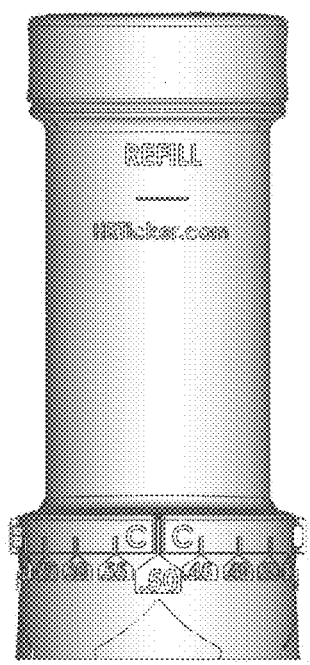
FIGS. 47-60 illustrate alternative embodiments of an apparatus for dispensing any flowable composition in reference to the various embodiments.
Figure 48:
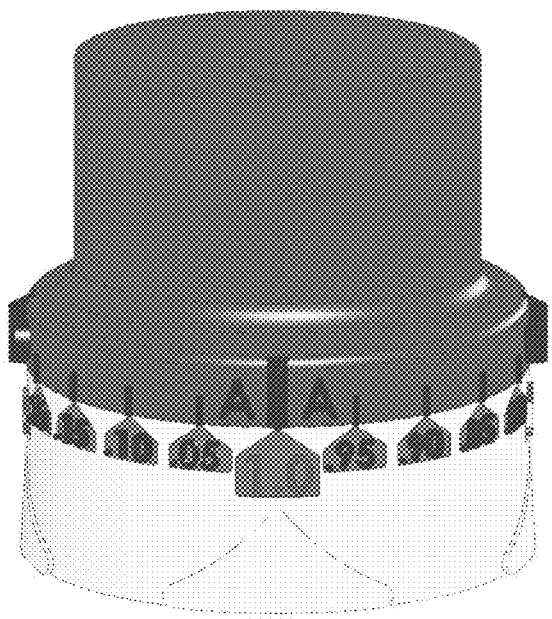
Figure 49:
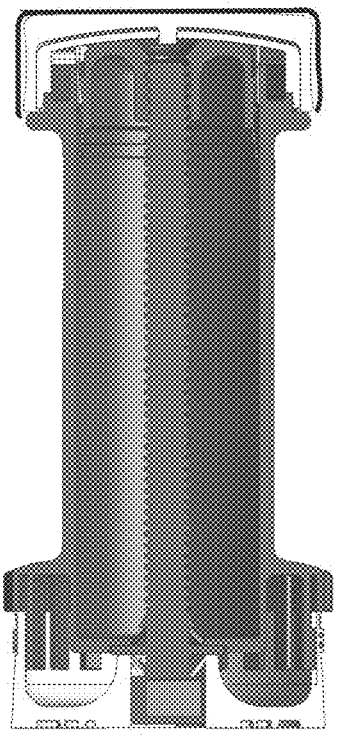
Figure 50:
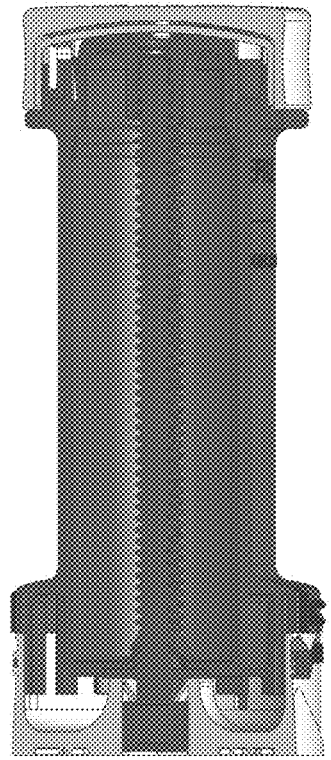
Figure 51:
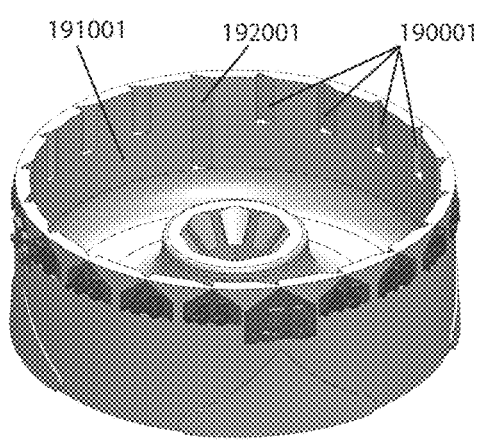
Figure 52:
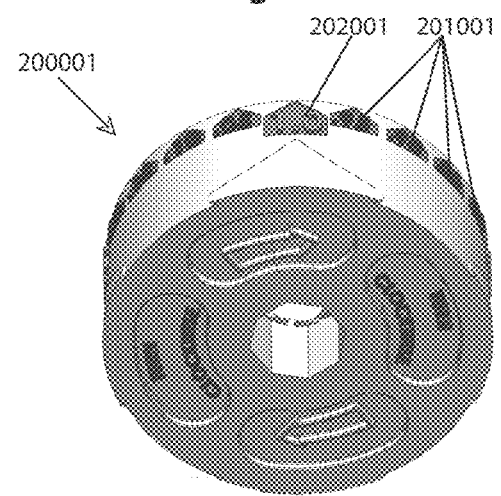
Figure 53:
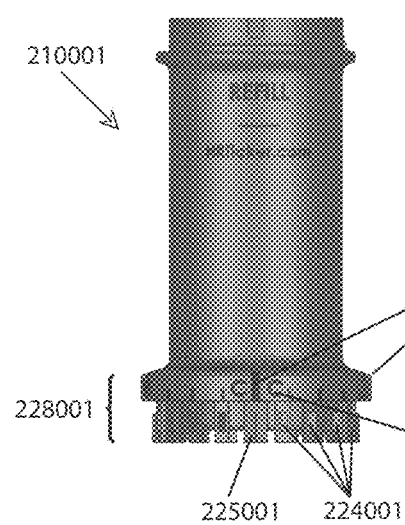
Figure 54:
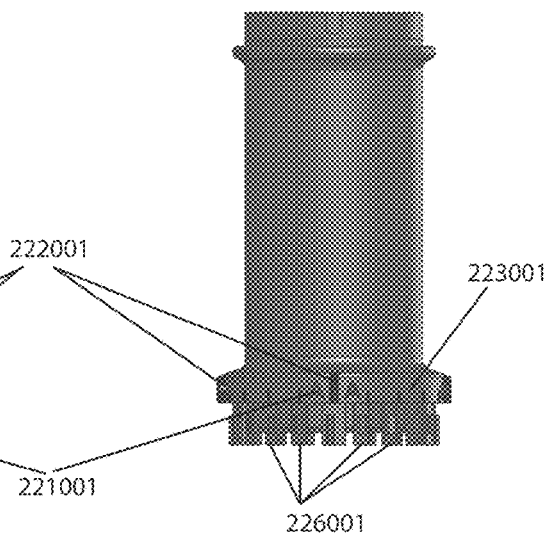
Figure 55:
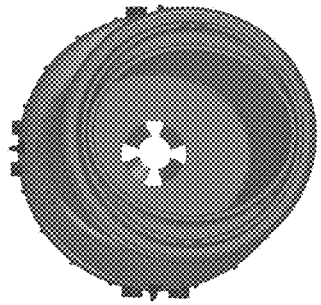
Figure 56:
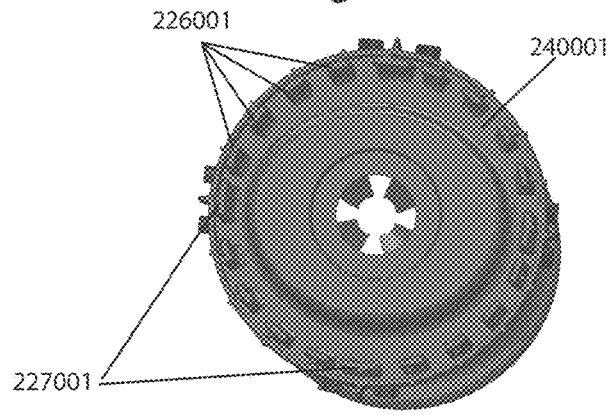

FIGS. 45 and 46 are schematic views of the safety cap 60001 exhibiting the top outer wall 60501, and smooth upper edge 61001, an outer side surface 61501, a lower edge 63501, an inner side wall 64001, an inner top wall 62001, a semi-annular rib 64501, reinforcement ribs 64601, and a plug 63001.

Pre-Assembly: This involves the collaboration four components; the screw-complex 20001, house 47001, elevator 32501 and rotatable platform 2501. The screw end 20101 and the screw-complex 20001 get inserted to the house 47001 past the house locking tabs 42501. Once the locking tabs 42501 override the snap ring 21001, the screw-complex 20001 gets trapped in the house 47001 in parallel with the chamber's inner side wall and it's only able to rotate axially. Tooling facilitates assembly of the elevator 32501 where counterclockwise rotation of the screw-complex 20001 allows the elevator 32501 to get screwed into the bottom end of the house 47001. The hexagonal shape of the bolt head 22001 allows it to be attached to an electrical female hexagonal-socket and yield assembly of the elevator 32501 into the bottom end of the house 47001 efficiently. Next, the rotatable platform 2501 is slipped into the bottom end of the house 47001 where the locking tabs 14501 overrides the bolt head 22001 to land into the bolt neck 23501 where the platform locking tabs 14501 secure the rotatable platform 2501 into the other said components (2501, 47001, 20001, 32501) in a tight fit, practically fusing the rotatable platform 2501 to the house-screw-complex-elevator components. The preassembled unit, along with the dispenser 50001, and security cap 60001, (assembly add-ons) can be shipped as a single unit or in large quantities.

Assembly: Compounding pharmacists or other dispensing personnel can place a desired quantity of the flowable cream-base medicament inside the chamber of the housing 47001 through the dispenser opening 40501. The dispenser 50001 gets positioned to fit into the housing 47001 through insertion guides 53001 that fit into the dispenser notch 47501*a*, 47501*b*. Upon pressing, the annular groove 54001 fastens into the peripheral rim 40701 of the house 47001. Once locked, the dispenser cannot be removed by the average consumer unless a skilled provider or technician, using a pointy tool can carefully pull the dispenser's bottom edge 52501 and displace the dispenser 50001 outwards. Once in place, the applicator gets primed (air removed) to a desired setting by rotating the rotatable platform clockwise; as allowed. We recommend technicians and dispensers to partially prime the unit to prevent spilling; especially if transporting to different altitudes as pressure changes may force the cream-base medicament out of the device. The security cap 60001 can be inserted to prevent medicament contamination, spill, and retard medicament evaporation by sealing the outlet 50501. The security cap 60001 can also be fastened to a tight fit if one applies additional force by cooperation of the semi-annular rib 64501 and safety rim 40801. A thumb tab 61101 is placed near the lower edge 63501 and lower outer side wall 61501 of the safety cap 60001 to ease removal.

Audible and Tactile Mechanism

Minor Tick Note: This is the sound and tactile sensation caused by the interaction of primary ticker tabs 43501 stemming from the bottom exterior wall 48001 of the house 47001 with minor side ticks 11001 stemming from the outer base rim 16001 of the rotatable platform 2501 due to an 18° displacement of the rotatable platform 2501 against the house 47001 to any predetermined minor digit tab (other than digit tabs 0.25, 0.50, 0.75, and 1.0). A soft and distinct sound and tactile sensation is captured by the user upon clockwise rotation of the rotatable platform 2501 against the house 47001 of the apparatus at any of these predetermined angular displacements allowed.

Major tick Note: This is the sound and tactile sensation caused by interaction of primary ticker tabs 43501 and major side ticks 11201 plus the concurrent interaction of secondary ticker tabs 44001 stemming from the bottom exterior wall 48001 of the house 47001 with redundant side ticks 11501 stemming from the inner base rim 15001 of the rotatable platform 2501 due to an 18° displacement of the rotatable platform 2501 with respect to the house 47001 to the following predetermined major digit tabs, 0.25, 0.50, 0.75, and 1.0. This summation, and thus amplification of sound and tactile sensations makes for a bi-audible and bi-tactile apparatus.

Refill Reminder Indicator: As presented on FIG. 37A, a small raised horizontal bar 47201 near the upper rim 41501 serves to indicate to the consumer their cream-base medicament may be running low. Further, the word, "refill" positioned right beneath the upper rim is shown embossed 47101 to also remind consumers their medicament may be running-out. A second raised horizontal line 47301 sits just about the middle part of the house 47001 to indicate pharmacy technicians or other dispensing personnel a rough estimation of a half-filled applicator in cases where the prescribed amount is half the usual amount prescribed, given that one full container may be the norm. There are two additional horizontal lines 47601, 47701 to also help in indicating levels of a 75% or a 100% composition-filled applicator; respectively. A vertical bar 47401, also shown in FIG. 37A, serves as a guide to properly position an indication label on the face of the outer side wall 4001 of the house 47001.

Variations

Figure 57:
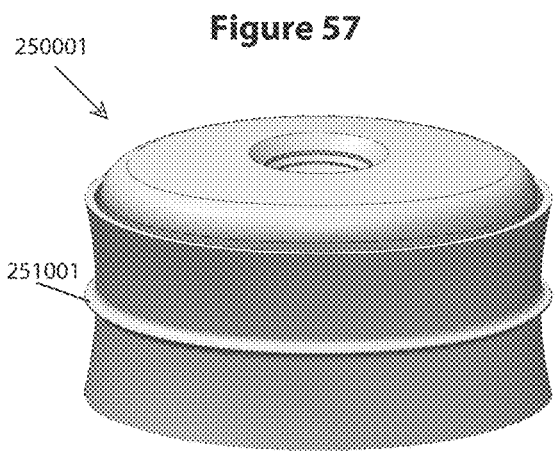
Figure 58:
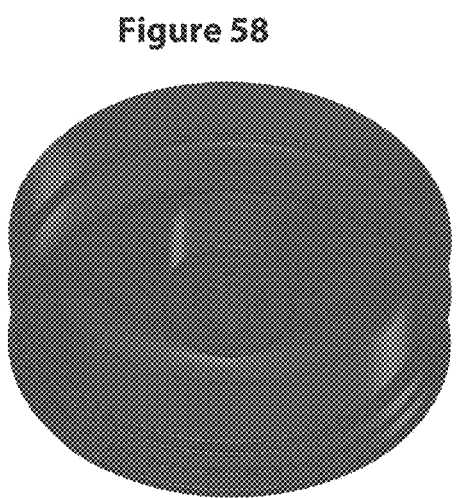
Figure 59:
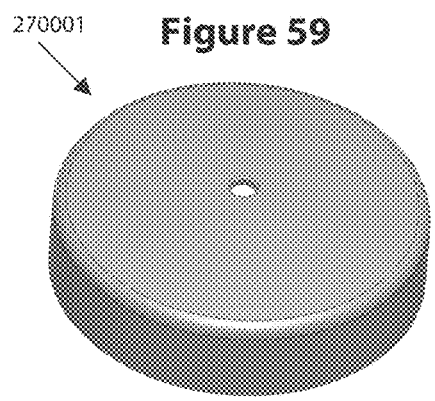
Figure 60:
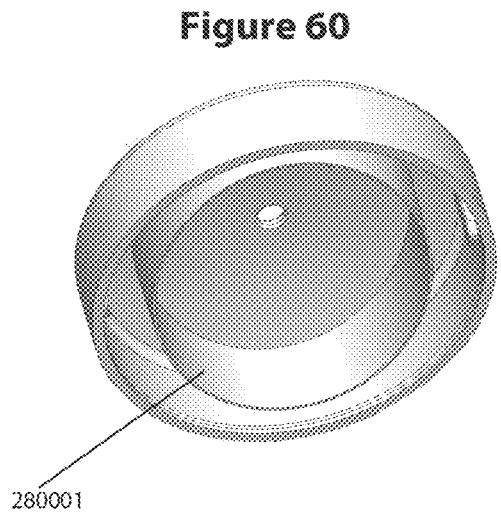

A variation of the current design is seen in on FIGS. 47-60 where the cream-base medicament is stored in an enclosed cylindrical shaped chamber. In addition, the major yielding tabs 227001, and minor yielding tabs 226001 emit a sound at every 18° rotation of the rotatable platform 200001 past the house member 210001. The main difference is that this device produces an almost identical sound and tactile sensation at every 18° rotation of the rotatable platform 200001 past the house member 210001. In addition, extruded grapheme letters 221001, (A,A, B,B, C,C, and D,D) and major line markings 222001 are located in the graduation ring 223001 of the platform end 228001 of the house 210001. The rotatable platform 200001 has four major slanted grooves 192001 and sixteen minor slanted grooves 190001 on the inner wall 191001 of the rotatable platform 200001 that engage with four major teeth-like projections 225001 and sixteen minor teeth-like projections 224001 stemming from four major yielding tabs 227001 and sixteen minor yielding tabs 226001 that originate from the bottom exterior wall 240001 of the house 210001; as seen on FIGS. 51-56. The Dispenser 270001 seen on FIGS. 59-60 has a slightly different inner slim wall 280001 to fit into said elliptical chamber where the composition is stored. The elevator 250001 with an enhanced mid-rim seal 251001 is seen on FIGS. 57 and 58 with its cylindrical shape configured to fit on the said house chamber. Each 18° rotation of the rotatable platform 200001 against the house 210001 is configured to deliver a ½₀th milliliter of flowable composition. A bi-tactile and bi-audible mechanism is also produced with this design. A first sound corresponding to digit tabs 0.25, 0.50, 0.75, and 1.0 is configured by increasing the depth of fall of major teeth-like projections 225001 into major slanted grooves 192001. A second sound at positions other than 0.25, 0.50, 0.75, and 1.0 is produced where the major teeth-like projections 225001 and minor teeth like projections 224001 land into minor slanted grooves 190001 where depth of fall of teeth-like projections into slanted grooves is rather shallow.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus comprising:
    a housing comprising a plurality of first tabs and a plurality of second tabs arranged at and stemming from a first end of the housing;

a rotatable platform coupled to the first end of the housing, the rotatable platform comprising a bottom wall, a side wall, and an inner base rim extending upward from an inner surface of the bottom wall within the rotatable platform,
  wherein the rotatable platform further comprises a plurality of first tab contacts extending upward from the inner surface of the bottom wall and radially outward from the inner base rim,
  and wherein the rotatable platform further comprises a plurality of second tab contacts extending upward from the inner surface of the bottom wall and radially inward from an inner surface of the side wall,
  and wherein the plurality of first tabs are configured to interact with the plurality of first tab contacts on the inner base rim and the plurality of second tabs are configured to interact with the plurality of second tab contacts on the rotatable platform when the rotatable platform is rotated relative to the housing;
a screw-complex in mechanical communication with the rotatable platform, wherein at least a portion of the screw-complex is positioned within an interior region of the housing;
an elevator in mechanical communication with the screw-complex, the elevator configured to move within the interior region of the housing when the rotatable platform is rotated relative to the housing; and
a dispenser coupled to a second end of the housing.

2. The apparatus of claim 1, wherein the rotatable platform is coupled to the first end of the housing such that at least one first tab of the plurality of first tabs is configured to contact and clear at least one first tab contact of the plurality of first tab contacts when the rotatable platform is rotated relative to the housing.

3. The apparatus of claim 2, wherein the at least one first tab contact interacts with the at least one first tab to produce a first sound when the rotatable platform is rotated relative to the housing by the predetermined amount.

4. The apparatus of claim 3, wherein at least one second tab contact interacts with at least one second tab to produce a second sound different from the first sound substantially simultaneously with the first sound when the rotatable platform is rotated relative to the housing by the predetermined amount.

5. The apparatus of claim 1, wherein the plurality of second tab contacts are substantially equispaced along the inner surface of the side wall of the rotatable platform.

6. The apparatus of claim 1, wherein the plurality of first tabs comprises four first tabs, the plurality of second tabs comprises two second tabs, the plurality of first tab contacts comprises four first tab contacts, and the plurality of second tab contacts comprises four second tab contacts.

7. The apparatus of claim 1, wherein the dispenser dispenses approximately 0.25 mL of composition per approximately 90° rotation of the rotatable platform.

8. The apparatus of claim 1, wherein each of the plurality of second tab contacts is taller than each of the plurality of first tab contacts.

9. The apparatus of claim 1, wherein the screw-complex comprises a hexagonally shaped bolt head and wherein the rotatable platform further comprises a plurality of locking tabs around a hexagonally shaped void configured to receive the hexagonally shaped bolt head.

10. The apparatus of claim 1, wherein each of the plurality of first tabs is longer than each of the plurality of second tabs.

11. The apparatus of claim 1, wherein the rotatable platform further comprises a receiver, and wherein at least a portion of the screw-complex is disposed within and is in mechanical communication with the receiver of the rotatable platform.

12. The apparatus of claim 11, wherein the receiver is disposed at a location within the inner base rim.

13. The apparatus of claim 12, wherein the receiver is disposed within an annulus of the inner base rim.

14. The apparatus of claim 1, wherein the inner base rim is substantially circular.

* * * * *